United States Patent [19]

Benkovic et al.

[11] Patent Number: 5,079,152

[45] Date of Patent: * Jan. 7, 1992

[54] ANTIBODY COMBINING SITES THAT EXHIBIT STEREOSELECTIVE SYNTHASE ACTIVITY, AND METHODS USING THE SAME

[75] Inventors: Stephen Benkovic, State College, Pa.; Richard A. Lerner, La Jolla, Calif.; Alfonso Tramontano, San Diego, Calif.; Andrew D. Napper, State College, Pa.

[73] Assignee: Scripps Clinic and Research Foundation, La Jolla, Calif.

[ * ] Notice: The portion of the term of this patent subsequent to Feb. 13, 2007 has been disclaimed.

[21] Appl. No.: 83,681

[22] Filed: Aug. 7, 1987

Related U.S. Application Data

[63] Continuation-in-part of Ser. No. 55,177, May 28, 1987.

[51] Int. Cl.$^5$ .............. C12P 17/06; C12N 9/88; C12N 9/00; C07K 15/28
[52] U.S. Cl. ............... 435/125; 435/232; 435/123; 530/387; 530/388
[58] Field of Search ........... 435/183, 196, 125, 232, 435/280, 129, 135; 530/387, 388, 389, 413

[56] References Cited

U.S. PATENT DOCUMENTS 4,659,567 4/1987 Tramontano et al. ............. 424/85
4,792,446 12/1988 Kim et al. ........................ 424/183

FOREIGN PATENT DOCUMENTS

WO8502414 6/1985 PCT Int'l Appl.

OTHER PUBLICATIONS

Proceedings of the XVIIIth Solvay Conference on Chemistry, Brussels, Nov. 28-Dec. 1, 1983, "Antibodies of Predetermined Specificity in Biology and Medicine", Richard Alan Lerner, pp. 43-49.
Jencks, W. P., "Catalysis in Chemistry and Enzymology", McGraw-Hill Book Company (1969), pp. 287-289.
Slobin, *Biochem.*, 5:2836-2844 (1966).
Kohen et al., *FEBS Letters*, 100:137-140 (1979).
Kohen et al., *Biochim. Biophys. Acta*, 629:328-337 (1980).
Kohen et al., *FEBS Letters*, 111:427-430 (1980).
Royer, *Adv. Catal.*, 29:197-227 (1980).
Jenks, *Adv. Enzymol.*, 43:313-317 (1975).
Lerner, *Adv. Imm.* 36:1-44 (1984).
Tramontano et al., *Proc. Natl. Acad. Sci. USA*, 83:6736-6740 (1986).
Pollack et al., *Science*, 234: 1570-1573 (1986).
Marx, *Science*, 234: 1497-1498 (1986).
Anon., *Chemical & Engineering News*, Dec. 15, 1986, p. 6.
Hansen, *Nature*, 325:304 (1987).
Anon., *Scientific American*, 256(2)(:84-85 (Feb. 1987).
Baum, *Chemical & Engineering News*, Apr. 6, 1987, pp. 30-33.
Napper et al., *Science*, 237:1041-1043 (1987).
Lerner et al., *TIBS*, 12:427-430 (1987).
Stinson, *Chemical & Engineering News*, Oct. 19, 1987, pp. 30-33.
Janda et al., *Science*, 241:1188-1191 (1988).
Marx, *Science*, 241:1164 (1988).

(List continued on next page.)

Primary Examiner—Elizabeth C. Weimar
Assistant Examiner—Charles L. Patterson
Attorney, Agent, or Firm—Dressler, Goldsmith, Shore, Sutker & Milnamow

[57] ABSTRACT

A phosphorus-containing analog-ligand having a stereoconfiguration that substantially corresponds to the stereoconfiguration of an amide- or ester-forming transition state is used to induce production of receptor molecules whose antibody combining sites have stereospecific amide or ester synthase catalytic activity when reacted with a ligand containing (i) a carbonyl carbon atom and (ii) an amine or alcohol group that are structurally capable of forming a preselected stereoisomer of a carboxylic amide or ester.

16 Claims, 5 Drawing Sheets

OTHER PUBLICATIONS

Anon, *Chemistry & Engineering News*, Sep. 5, 1988, p. 14.
Vogel, *Discover*, 9:38-43 (Oct. 1988).
Massey, *Nature*, 328:457-458 (Jul. 1987).
Tramontano et al., *J. Am. Chem. Soc.*, 110:2282-2286 (1988).
Janda et al., *J. Am. Chem. Soc.*, 110-4835-4837 (1988).
Benkovic et al., *Proc. Natl. Acad. Sci. USA.*, 85:5355-5358 (Aug. 1988).
Tramontano et al., *Science*, 234:1566-1570.
White et al., *Principles of Biochemistry*, McGraw-Hill Book Company, New York (1978), p. 202.
Hogness et al., *Qualitative Analysis and Chemical Equilibrium*, 4th ed., Holt, Reinhart and Winston, Inc., New York (1954), p. 565.
Raso et al., *J. Am. Chem. Soc.*, 95(5):1621-1628 (1973).
Computer Print-Out—B. D. Sollar—123 papers and abstracts.
Computer print-out—V. Raso—13 papers and abstracts.
Raso et al., *Biochem.*, 14(3):591-599 (1975).
Raso et al., *Biochem.*, 14(3):584-591 (1975).

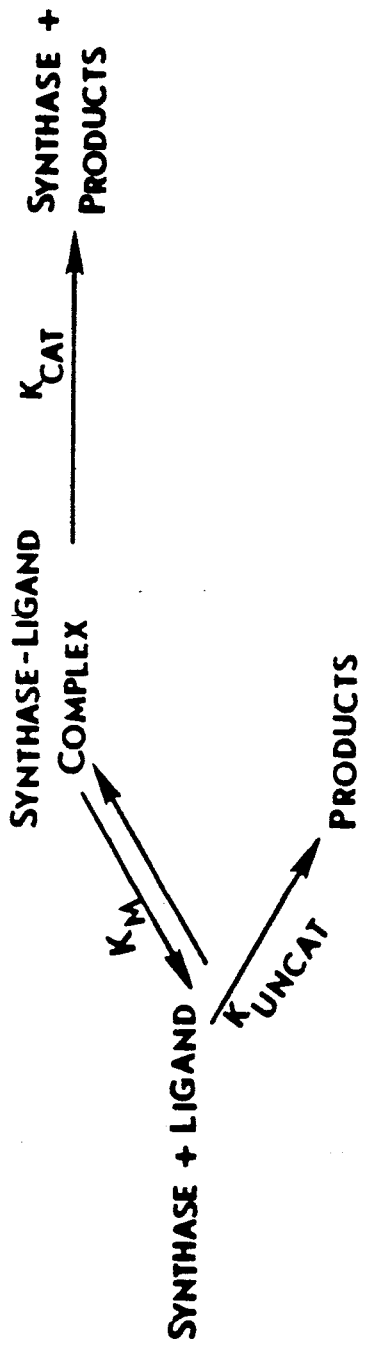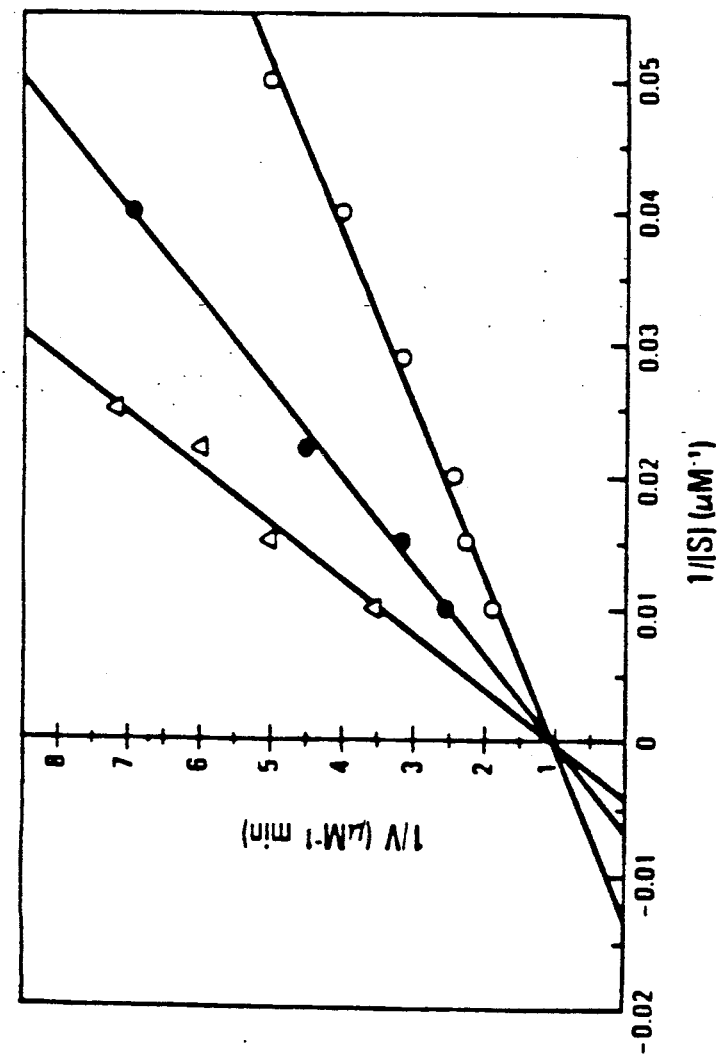
FIGURE 3

ANTIBODY COMBINING SITES THAT EXHIBIT STEREOSELECTIVE SYNTHASE ACTIVITY, AND METHODS USING THE SAME

This invention was made with the support of the United States Government, and the United States Government has certain rights in the invention.

CROSS-REFERENCE TO RELATED APPLICATION

This is a continuation-in-part of co-pending application Ser. No. 055,177 filed May 28, 1987 now U.S. Pat. No. 4,900,674 whose disclosures are incorporated by reference.

TECHNICAL FIELD

The present invention relates to antibodies (receptors), antigens and immunogens (ligands), and more particularly to receptor molecules that contain an antibody combining site that stereospecifically binds and thereby stabilizes a transition state leading to a stereospecific product and exhibits catalytic properties, as well as to use of such receptors to separate stereoisomers.

BACKGROUND OF THE INVENTION

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding can lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively. In addition, such binding can lead to formation of amide and ester bonds in the formation of proteins and fats, as well as to the formation of carbon to carbon bonds and carbon to nitrogen bonds.

Immunological binding can be used to experimentally divert binding interactions to catalytic processes. Jencks, W. P., *Catalysis in Chemistry and Enzymology*, page 288 (McGraw-Hill, New York 1969). Attempts to introduce reactive groups into a combining site of an antibody, however, have generally been unsuccessful. Royer, G. P., *Adv. Catal.*, 29, 197 (1980). Some monoclonal antibodies are reported to include nucleophilic residues that react with an activated ester appendage on a homologous hapten recognized by the antibody. Kohen et al., *FEBS Lett.*, 111, 427 (1980); Kohen et al., *Biochem. Biophys. Acta*, 629, 328 (1980) and Kohen et al., *FEBS Lett.*, 100, 137 (1979). In these cases, the rate of acylation of the nucleophile is presumably accelerated by its proximity to a binding site of the haptenic fragment.

These constructs, though interesting, are severely limited by their failures to address the mechanism of binding energy utilization that is essential to enzymes [W. P. Jencks, *Adv. Enzymol.*, 43, 219 (1975)]. Aside from that failure, when strong binding is directed to stable states, the slow rate of dissociation of the complex can impede catalysis.

The above deficiencies can be redressed by using a transition state analog as the hapten to elicit the desired antibodies. This hapten (also referred to herein as an "analog-ligand") can assume the role of an inhibitor in the catalytic system.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful, well-accepted mental constructs that by definition, cannot be isolated, as compared to intermediates, which can be isolated.

Although the above hydrolytic and other transition states can not be isolated, a large amount of scientific literature has been devoted to the subject. Some of that literature is discussed hereinafter.

Whereas the before-described transition state for amide and ester hydrolyses is believed to be well understood, the parameters of the topology, e.g., size, shape (stereoconfiguration) and charge, of receptor binding sites in which particular amides, such as proteins, or esters, such as fats, react through those transition states is not as well understood. It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose locations are known, the chemical identity; i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. Although such relatively random cleavage can be useful in obtaining a polypeptide map of the protein, that relatively random cleavage is not as useful where particular amino acid residue sequences are desired to be produced.

Recently, Lerner, Tramontano and Janda [*Science*, 234, 1566 (1986)] reported monoclonal antibodies that catalytically hydrolyzed an ester. Tramontano and Lerner, also describe using monoclonal antibodies to hydrolyze esters in U.S. Pat. No. 4,656,567. Pollack, Jacobs and Schultz [*Science*, 234, 1570 (1986)] reported a myeloma protein denominated MOPC167 [Leon et al., *Biochem.*, 10, 1424 (1971)] that catalyzes the hydrolysis of a carbonate.

In the two Lerner and Tramontano disclosures, the antibodies were raised to a phosphonate that was synthesized to represent a stable analog of the tetrahedral hydrolytic transition state of the carboxylic acid ester or amide. The Pollack et al. antibody principally discussed was a myeloma protein that happened to bind to a phosphonate that was structurally analogous to the carbonate analog hydrolyzed. Thus, in the Lerner and Tramontano et al. work, the substrate to be hydrolyzed was preselected, with the immunizing analog and hydrolytic antibodies being synthesized in accordance with the desired product. Pollack et al. designed the substrate to be hydrolyzed once they knew the specificity of the myeloma protein. Pollack et al. also reported (above) the existence of a catalytic antibody, substrate and analog substrate system for carbonate hydrolysis similar in concept to that of Lerner et al. Work relating to that system is reported in Jacobs et al., *J. Am. Chem Soc.*, 109:2174 (1987).

Published patent application WO 85/02414 discusses the possible use of antibodies as catalysts, and presents data relating to the use of polyclonal serum in hydrolyzing o-nitrophenyl-beta-D-galactoside. The antibodies useful in that application are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turn over of the allegedly catalytic antibody was shown, nor was there an indication of the percentage of substrate galactoside cleaved. That application did indicate that beta-D-galactosidase cleaved about ten times as much substrate as did the polyclonal antibodies, presuming linearity of absorbance at the unnamed concentration of substrate studied.

From the data presented in that application, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

BRIEF SUMMARY OF THE INVENTION

The present invention contemplates a catalytic molecule. That molecule contains an antibody combining site that itself constitutes the catalytically active portion of the molecule. An antibody combining site can also be referred to as a paratope or an idiotype-containing polyamide. The catalytic molecule is generally referred to herein as a receptor molecule, or more simply, a receptor.

A receptor molecule of the present invention is preferably monoclonal (discussed hereinafter), and contains an antibody combining site that is capable of catalyzing the formation of a preselected bond such as a carboxylic amide or ester bond, preferably a lactone bond.

In enzymology, a protein that catalyzes a bond-forming reaction can be referred to as a synthase. A protein that catalyzes an amide- or ester-forming reaction can be said to be a member of the amide or ester synthase family of enzymes. Using that nomenclature system for the preferred formation of a lactone, a lactone-forming enzyme can be referred to as a lactone synthase. The receptors of this invention will be described herein as exhibiting synthase activity when discussed broadly, amide or ester synthase activity when discussed at intermediate breadth, and will be described as exhibiting lactone synthase activity when discussed in relation to the specific reactions described herein as exemplary.

The synthesis reactions discussed herein are preferably stereospecific. By stereospecific (or stereoselective) it is meant that one of at least two stereoisomers is formed preferentially in the reaction.

Stereoisomers can be geometric isomers such as cis and trans isomers or optical isomers that are also called enantiomers. Geometric and enantiomeric isomers can also exist in the same molecule, particularly molecules containing rings, and such stereoisomers are also contemplated.

A receptor capable of catalyzing stereoselective synthesis is contemplated herein. Such a stereoselective synthase molecule is preferably monoclonal and catalyzes the synthesis of a preselected product that contains relatively more of one stereoisomer than the other stereoisomer.

The stereoselective receptor synthase molecule contains an antibody combining site capable of catalyzing the stereoselective synthesis of a desired product. That antibody combining site binds to substantially only one stereoisomer (geometric or optical) of a reactant ligand that is structurally capable of forming the product, and also binds to substantially only one stereoisomer of a ligand structurally analogous (analog-ligand) to a transition state leading to one stereoisomer of the product. Thus, for example, the receptor binds selectively to one enantiomer of the analog-ligand, and to one enantiomer of the reactant ligand to preferentially form one enantiomer of the product, where enantiomers are the stereoisomers of interest.

The present invention also contemplates a molecule exhibiting amide or ester synthase activity that comprises a receptor molecule. The preferably monoclonal receptor contains an antibody combining site capable of catalyzing the formation of a preselected carboxylic amide or ester bond. The combining site binds to: (a) a reactant ligand containing a carbonyl group carbon atom and an amine or alcohol group that is structurally capable of forming the preselected carboxylic amide or ester bond (the reactant ligand); and (b) a ligand structurally analogous to the preselected amide or ester; the analog-ligand having a tetrahedrally bonded phosphorus atom located at the position occupied by the above-mentioned carbonyl carbon atom of the preselected carboxylic amide or ester bond of the before-mentioned ligand. The tetrahedrally bonded phosphorus atom is itself directly bonded to: (i) the alpha-carbon atom of the acid portion of the analog ligand by a single bond; (ii) a first oxygen atom that is doubly bonded to the phosphorus atom; (iii) a second oxygen atom that is bonded to the phosphorus atom by a single bond, and is singly bonded to a radical selected from the group consisting of hydrogen, $C_1$-$C_6$ lower alkyl, benzyl and phenyl; and (iv) a third oxygen atom or a nitrogen atom singly bonded to the phosphorus atom, and is also singly bonded to the alpha-carbon atom of the amine or alcohol portion of the analog ligand.

A receptor capable of catalyzing the formation of an excess of a preselected enantiomeric carboxylic acid amide or ester product such as a lactam or a lactone over the other enantiomer is further contemplated. Here, the receptor amide or ester synthase contains an antibody combining site capable of catalyzing the formation of a preselected enantiomer of the amide or ester product, and the combining site binds to: (a) substantially only one of a ligand enantiomeric pair that contains a carbonyl group carbon atom and an amine or alcohol group structurally capable of forming the preselected amide or ester (reactant ligand enantiomer), and (b) a ligand structurally analogous (analog-ligand) to one enantiomer of a transition state leading to the preselected amide or ester product.

The analog-ligand contains a tetrahedrally bonded phosphorus atom located at the position occupied by the carbon atom of the carbonyl group of the preselected carboxylic amide or ester product. That tetrahedrally bonded phosphorus atom being bonded directly to: (i) the alpha-carbon atom of the acid portion of the analog-ligand by a single bond; (ii) a first oxyen atom that is doubly bonded to the phosphorus; (iii) a second oxygen atom that is bonded to said phosphorus atom by a single bond, and is singly bonded to a radical selected from the group consisting of hydrogen, $C_1$-$C_6$ lower alkyl, benzyl and phenyl; and (iv) a third oxygen atom or a nitrogen atom that is singly bonded to the phosphorus atom, and is also singly bonded to the alpha-carbon atom of the alcohol or amine portion of the analog-ligand.

In preferred practice, the receptor molecule exhibits stereoselective lactam or lactone synthase activity. A particularly preferred synthase molecule is the monoclonal antibody denominated 24B11. Thus, the reactant ligand containing the carbonyl carbon is capable of forming a lactone, and the analog ligand is a cyclic phosphonate. In particularly preferred practice, the ligand and analog-ligands have structures of formulas I and II, respectively, below:

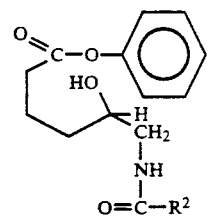

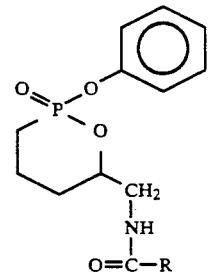

wherein R is hydrogen, $C_1$-$C_6$ lower alkyl or a linking group bonded to an antigenic carrier; and $R^2$ is hydrogen or $C_1$-$C_6$ lower alkyl, and the receptor preferentially immunoreacts with one enantiomer of the ligand and one enantiomer of the analog-ligand.

A method for carrying out a stereoselective synthesis to prepare a preselected product that contains relatively more of one stereoisomer than another stereoisomer is contemplated as another aspect of the invention. For this synthesis, a reactant ligand and an effective amount of a synthase molecule are admixed in an aqueous medium to form a reaction medium; the reactant ligand being structurally capable of forming two stereoisomers of the desired product. The synthase molecule comprises a receptor molecule, preferably monoclonal, that contains an antibody combining site capable of stereospecifically catalyzing the formation of the product. That antibody combining site binds to: (a) substantially only one stereoisomer of the ligand, and (b) a ligand structurally analogous to a transition state leading to one stereoisomer of the product (analog-ligand).

The reaction mixture is maintained for a period of time sufficient for the stereoisomeric product to form. The product, containing relatively more of one stereoisomer; i.e., the stereoisomer whose formation was catalyzed by the synthase molecule, than another stereoisomer is thereafter typically recovered.

Another embodiment contemplates a method for forming (synthesizing) a preselected enantiomeric carboxylic acid amide or ester product that contains an excess of one enantiomer over the other enantiomer. Here, an enantiomeric reactant ligand pair structually capable of forming the enantiomeric carboxylic amide or ester is admixed with an effective amount of an amide or ester synthase molecule to form a reaction mixture. The reactant ligand contains a carbonyl group carbon atom and an amine or alcohol group capable of forming the preselected carboxylic acid amide or ester product. The amide or ester synthase molecule comprises a receptor molecule, preferably monoclonal, that contains an antibody combining site capable of catalyzing the formation of the preselected enantiomer of the amide or ester product.

That combining site binds to: (a) substantially only one enantiomer of the enantiomeric reactant ligand pair, and (b) a ligand structurally analogous to one enantiomer of a transition state leading to the preselected amide or ester product. The enantiomer of the analog-ligand that is bound by that combining site has a tetrahedrally bonded phosphorus atom located at the position occupied by the carbon atom of the carbonyl group of the carboxylic acid amide or ester product.

The tetrahedrally bonded phosphorus atom of the analog ligand is bonded directly to: (i) the alpha-carbon atom of the acid portion of the analog-ligand by a single bond; (ii) a first oxygen atom that is doubly bonded to the phosphorus atom; (iii) a second oxygen atom that is singly bonded to the phosphorus atom, and is singly bonded to a radical selected from the group consisting of hydrogen, $C_1$–$C_6$ lower alkyl, benzyl and phenyl; and (iv) a third oxygen atom or a nitrogen atom that is singly bonded to the phosphorus atom, and is also singly bonded to the alpha-carbon atom of the amine or alcohol portion of the analog-ligand.

The reaction mixture is maintained for a time period sufficient for the preselected amide or ester product enantiomer to form. The product is thereafter again typically recovered containing an excess of one enantiomer over the other.

A method of forming a preselected carboxylic acid amide or ester constitutes still another aspect of the present invention. Here, a ligand containing a carbonyl group carbon atom and an amine or alcohol group structurally capable of forming the preselected carboxylic acid amide or ester is admixed in an aqueous medium with an effective amount of an amide or ester synthase molecule to form a reaction mixture. Here, however, the reactant ligand and analog-ligand need not have stereoisomers, nor need the product have stereoisomers. The reaction mixture is thereafter maintained for a time period sufficient for the amide or ester to form; and the product is thereafter preferably recovered.

The invention contemplates a reactant ligand structurally capable of forming an amide or ester as well as an analog-ligand containing an analog to the amide- or ester-forming transition state leading to the amide or ester product. Those molecules differ in the fact the ligand contains a carbonyl group and an amine or alcohol capable of forming an amide or ester, whereas the analog-ligand contains a phosphorus central atom in a structure that mimics the amide- or ester-forming transition state. The ligand and analog-ligand can also differ in the substitution of the atoms bonded to the central atom at a position at least one atom away from the central atom since the analog-ligand must possess sufficient stability to be used as an immunizing hapten, and be bound to an antigenic carrier.

In the studies described herein, phosphonate monoaryl esters function as transition state analogs to generate antibodies that exhibit amide or ester synthase activity, and specifically, stereoselective lactone synthase activity. In effect, these antibodies express their inherent binding energy functionally, as true enzymes, to form an amide (lactam) or ester (lactone), and classically, as antibodies, to bind antigens.

An exemplary immunizing analog-ligand molecule that constitutes an analog of a lactone-forming transition state is represented by a compound having a structure of formula III:

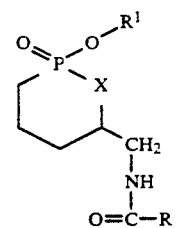

wherein
X is O or NH;
R is hydrogen, $C_1$–$C_6$ lower alkyl, or a linking group alone or bonded to an antigenic carrier; and
$R^1$ is hydrogen, $C_1$–$C_6$ lower alkyl, benzyl or phenyl.

The analog-ligand transition state molecules contemplated in this invention are of relatively small molecular size, as compared to a protein, and are therefore typically linked to a larger, antigenic carrier molecule when used to induce the production of a receptor molecule. Such relatively small molecules are commonly referred to as haptens. These analog-ligand molecules also typically contain a linking atom or group such as a reactive mercaptan, a succinimide or activated carbonylic acid ester group that provides a means to attach the haptenic analog-ligand molecules to an antigenic carrier for use as an immunogen, as shown in the formula above.

A method of preparing a synthase molecule such as an amide or ester synthase is also contemplated. Here, a before-described haptenic analog-ligand molecule that comprises a transition state analog of the product to be formed such as an amide- or ester-forming transition state analog is provided linked to an antigenic carrier as an immunogenic conjugate. The conjugate thus provided is dissolved or dispersed in a physiologically tolerable diluent to form an inoculum. The inoculum is introduced as by injection into a mammalian host such as a laboratory animal or a horse in an amount sufficient to induce antibodies to the haptenic analog-ligand. The antibodies so induced are harvested. The harvested antibodies that immunoreact with the immunizing, haptenic analog-ligand and catalyze the desired reaction are then collected.

In particularly preferred practice, monoclonal antibodies are prepared. Here, the above immunizing technique is used and the harvested antibodies are assayed for their ability to bind to (immunoreact with) the immunizing, haptenic ligand analog. Immunoglobulin-producing cells such as those from the spleen of an animal whose antibodies bind to the immunizing, haptenic analog-ligand are collected and are fused with myeloma cells to form hybridoma cells. The hybridoma cells are grown in a culture medium and the supernatant medium from the growing hybridoma cells is assayed for the presence of antibodies that bind to the immunizing, haptenic analog-ligand and catalyze the desired reaction of the reactant ligand. Hybridoma cells whose supernatant contains such binding, catalytic antibodies are then cloned to provide the desired monoclonal antibodies from culture medium supernatant or from the ascites of another host mammal into which the hybridoma is introduced.

Where the analog-ligand is capable of exhibiting stereoisomerism, the monoclonal antibodies selected preferably immunoreact stereospecifically with one of those stereoisomers in preference to another stereoisomer. For example, the analog-ligand whose structure is depicted in formula III has a chiral carbon atom at the position at which the side chain joins the ring and therefore exists as an enantiomeric pair, unless the racemic modification is resolved. A particularly preferred lactone synthase of this invention, the monoclonal antibody secreted by hybridoma 24B11, stereoselectively immunoreacts with one of those enantiomers as compared to the other, as is the case for the corresponding reactant ligand, and thereby preferentially catalyzes formation of one enantiomeric product over the other enanitomer.

The described polyclonal or monoclonal antibodies can be used as the synthase molecules of this invention. Alternatively, the so-called Fc or Fc' portions of the antibodies can be removed as by enzymic cleavage to provide an antibody combining site (paratope or idiotype-containing polyamide) that binds to the immunizing, haptenic analog-ligand such as Fab or F(ab')$_2$ antibody portion, respectively.

The polyclonal, monoclonal and idiotype-containing polyamide receptors also bind to the reactant ligand capable of forming the desired product such as an amide or ester. Such binding typically leads to catalyzed formation of the preselected bond, e.g., the amide or ester bond.

Still another embodiment of the present invention is a method for separating one of a pair of stereoisomers from the other. In this aspect, a receptor molecule, preferably monoclonal, is admixed with a pair of stereoisomers in an aqueous medium to form an admixture. This receptor contains an antibody combining site that immunoreacts stereoselectively with substantially only one of the stereoisomers. The admixture so formed is maintained for a time period sufficient for the receptor to immunoreact with (bind to) one of the stereoisomers to form an immunoreactant within the admixture. The immunoreactant is thereafter separated from the remaining admixture, thereby separating one of the stereoisomers from the other. The bound stereoisomer can be separated from the receptor of the immunoreactant in a further step.

The present invention provides several benefits and advantages. One benefit is the preparation of receptors whose binding site topological requirements are tailored to a particular ligand to be studied.

Another benefit of the present invention is the preparation of receptors that form an amide or ester bond at a predetermined site and that exhibit catalytic properties.

An advantage of the invention is that because of the specificity of the receptors that are produced, a reactant ligand containing a plurality of different reactive groups capable of forming bonds can be caused to form the desired bond at a preselected, particular site.

Another advantage of the present invention is that it provides a means for stereoselective syntheses.

Still another benefit of the invention is that one enantiomeric product can be prepared in excess over the other enantiomer.

Still another advantage of the invention is that is provides a method for separating stereoisomers such as enantiomers that is far easier than previously known techniques.

Still further benefits and advantages of the present invention will be apparent to those skilled in the art from the disclosures that follow.

BRIEF DESCRIPTION OF THE DRAWINGS

In the drawings, which constitute a portion of this disclosure:

FIG. 3 contains two portions. The upper portion is a schematic depiction of the catalyzed lactone-formation reaction between a lactone synthase and a reactant ligand using a usual Michaelis-Menten depiction. As is shown, the synthase and reactant ligand can reversibly form a complex analogous to an enzyme-substrate complex. The equilibrium constant for the formation is the Michaelis constant, $K_m$. That complex can go on to form products and a regenerated synthase molecule via the rate constant for the catalyzed reaction, $k_{cat}$. The reactant ligand is also shown as forming products by an uncatalyzed reaction with an uncatalyzed rate constant, $k_{uncat}$. The lower portion of the figure is a graph showing three Lineweaver-Burk plots derivable from a Michaelis-Menten depiction for cyclization of the reactant ligand of FIG. 1, where R is methyl, catalyzed by the monoclonal receptor lactone synthase molecule secreted by hybriodoma 24B11. Velocities were determined spectrophotometrically by measuring the initial linear absorbance change at 271 nanometers (nm).

The receptor [present at 2 micromolar (uM), as determined by Lowry assay, using a molecular weight of 150,000 daltons for an IgG molecule] was maintained in solution at 25 degrees C. prior to addition of the substrate reactant ligand. Reactions were initiated by addition of varying aliquots of a stock solution of reactant ligand substrate to provide a substrate concentration of 20–100 uM. The substrate stock solution was prepared by deprotection of the trimethylsilyl derivative using 5 percent citric acid in methanol, followed by dilution with 25 mM phosphate buffer, pH 7.0, to provide the desired concentration of stock solution. The prepared stock solution as stored frozen at −80 degrees C. until immediately prior to use.

The first order rate constant ($k_{uncat}$) for the cyclization in the absence of receptor molecules was measured similarly and used to correct the initial rate data.

Figure 1:
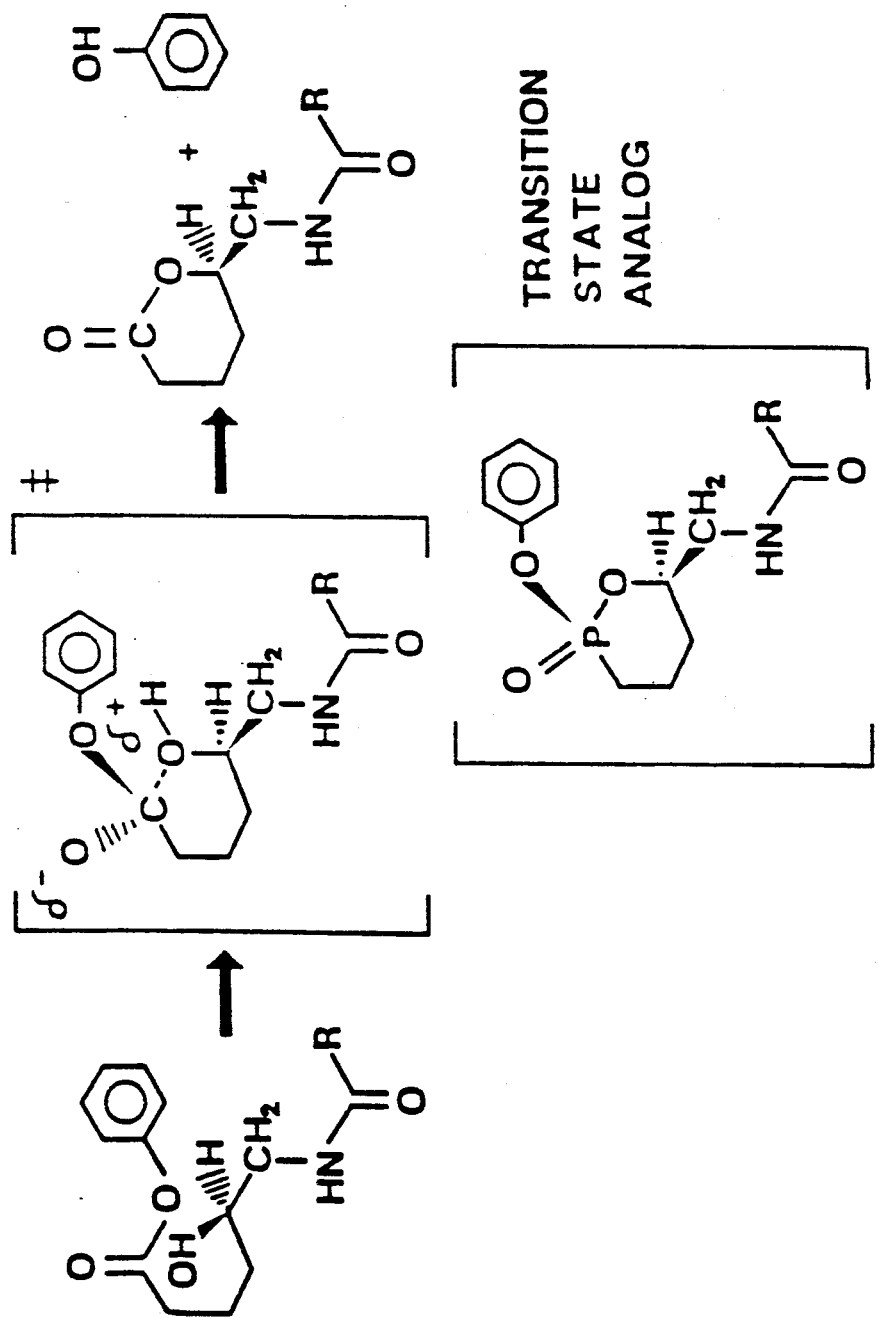
FIG. 1 is a schematic representation showing a reactant ligand structurally capable of forming a lactone (on the left), a proposed lactone-forming transition state for the ligand (bracketed, upper center), a structure of the analog-ligand (bracketed, lower center), and the lactone product of the reaction (on the right). The stereoconfigurations of one ligand enantiomer, the transition state, analog-ligand, and product are illustrated to show one possible stereochemical pathway. In that stereochemical view, solid lines are in the plane of the page, bonds projecting outwardly from the page are shown by solid triangular bonds, bonds projecting backwardly from the page are shown by a dashes, and a bond being formed is shown as a dotted line. The symbols $\delta-$ and $\delta+$ are utilized to show relative negative and positive charges, and the symbol $\neq$ designates the transition state.

The data shown in the graphs are for the reaction with no inhibitor present (open circles), the reaction inhibited by 0.25 uM of the N-acetyl derivative of the analog-ligand of FIG. 1 (R is methyl; closed circles), and the reaction inhibited by 0.50 uM of the same N-acetyl derivative of the analog-ligand.

The ordinate is in units of reciprocal initial velocity, 1/V, in minutes per micromole ($uM^{-1}$ min) The abscissa is in units of reciprocal substrate concentration, 1/[S], in $micromoles^{-1}$ ($uM^{-1}$).

Figure 4:
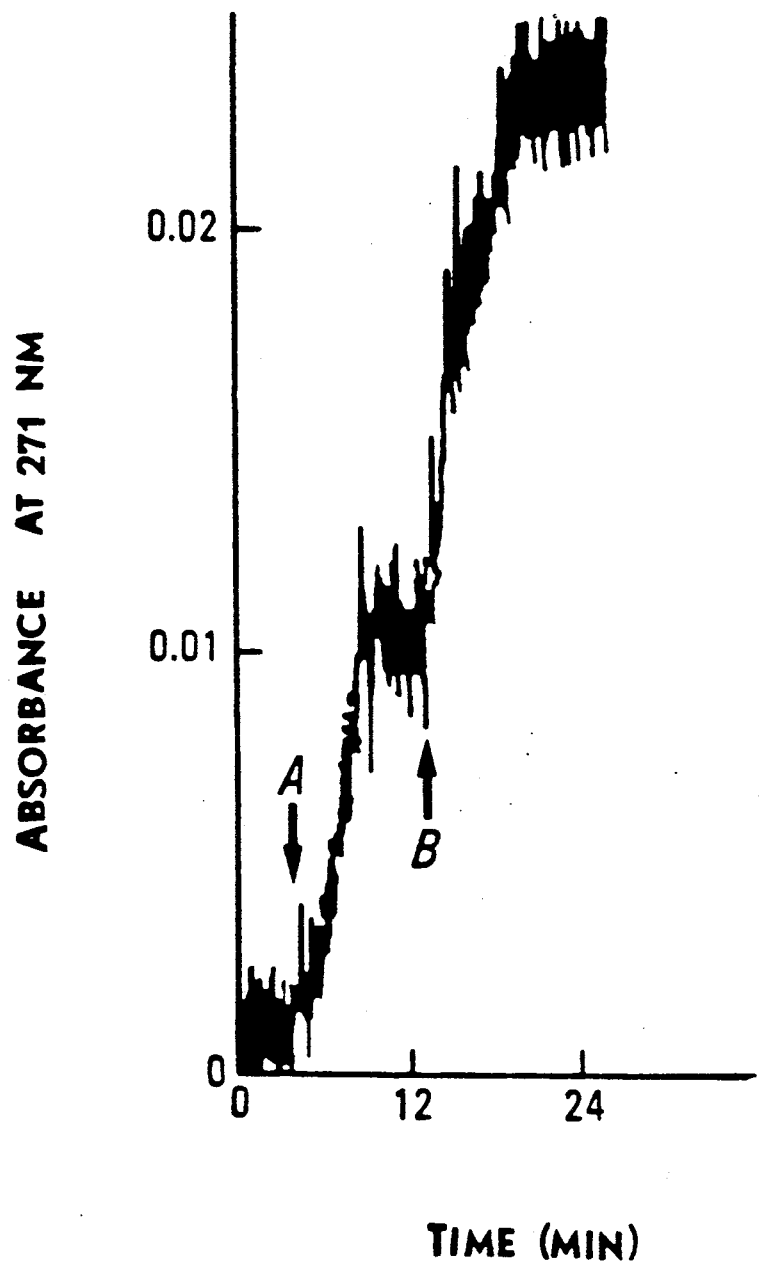

FIG. 4 is an exemplary graph illustrating the absorbance at 271 nm on the ordinate versus time in minutes (min) for the cyclization of the reactant ligand of FIG. 3 catalyzed by the monoclonal receptor lactone synthase molecule secreted by hybridoma 24B11.

The receptor was present at 20 uM in 25 mM phosphate buffer,, pH 7.0, at 25 degrees C. An aliquot of the ligand (present at 3.34 mM in phosphate buffer, pH 7.0) calculated to provide a 40 uM solution of the ligand was added to the receptor solution at each of points A and B of the graph.

The average observed absorbance increase was shown to correspond to consumption of 49±13 percent of the ligand after each injection, relative to a phenol standard.

Figure 5A:
Figure 5B:
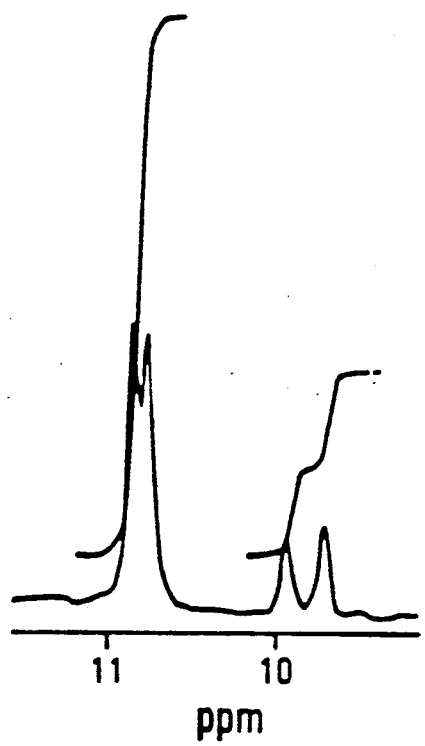

FIG. 5 contains two graphs (A and B) that are portions of $^1$H nuclear magnetic resonance (NMR) spectra of the lactone product of FIG. 1, where R is methyl. The spectra were obtained in $CDCl_3$ at 360 MHz in the presence of about one equivalent of the chiral lanthanide shift reagent tris[heptafluoropropylhydroxymethylene)-d-camphorato]-europium (III). Chemical shifts are shown in parts per million (ppm) downfield from tetramethylsilane (TMS).

Peak assignments (δ) and chemical shift differences between enantiomers (ΔΔδ) were determined as follows: Graph A δ9.45 and 9.68 (one of the $CH_2\underline{N}HCOCH_3$, ΔΔδ=0.23) δ10.60 and 10.67 (NH$\underline{COCH_3}$, ΔΔδ=0.07); Graph B δ9.71 and 9.94 (one of $C\underline{H_2}NHCOCH_3$, ΔΔδ=0.23; δ10.74 and 10.82 (NH$\underline{COCH_3}$, ΔΔδ=0.08).

For Graph A, the lactone was obtained by cyclization of the corresponding reactant ligand substrate for 55 minutes at 25° C. in 25 mM phosphate buffer, pH 7, in the presence of the lactone synthase receptor molecule secreted by hybridoma 24B11, at an initial ratio of reactant ligand substrate to receptor molecule of 9.2 mM:115 uM. For Graph B, the lactone was obtained under the same reaction conditions, but without the presence of the lactone synthase receptor molecule. When present, the receptor molecule was removed by Centricon filtration, followed by methylene chloride extraction of the filtrate and column chromatography on silica thereafter.

DETAILED DESCRIPTION OF THE INVENTION

I. Introduction production of antibodies and idiotype-containing polyamide (antibody combining site) portions induced by an analog-ligand that mimics the stereoconfiguration of a transition state in the reaction sequence for the formation of a chemical bond such as an ester or an amide bond, and particularly to the formation of a lactone bond. The antibodies and idiotype-containing polyamides bind to the amide- or ester-forming transition state of a preselected portion of a ligand and exhibit catalytic properties.

Antibodies and enzymes are both proteins whose function depends on their ability to bind specific target molecules. Enzymatic reactions differ from immunological reactions in that in ar enzymatic reaction the binding of the enzyme to its substrate typically leads to chemical catalysis, whereas a non-catalytic complex is the usual result of antibody-antigen binding.

Enzymes are believed to catalyze the reactions of proteins or other substrates by combining with the protein (substrate) to stabilize the transition state of the reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W. P., *Adv. Enzymology*, 43, 219 (1975) and Pauling, L., *Amer. Scientist*, 36, 58 (1948)]. Support for this theory comes from the observation that substances that are thought to model the presumed transition states are often strongly bound to the enzymes as competitive inhibitors. Leinhard, G., *Science*, 180, 149 (1973) and Wolfenden, R., *Acc. Chem. Res.*, 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., *XVII International Solvay Conference* (November 1983)].

The converse proposition is that a receptor that is prepared to optimally bind a suitable analog of a transition state would function as a catalyst. The demonstration of this result as shown herein completes the correlation of enzyme function and receptor structure, and provides a useful approach to devising artificial enzymes.

The basic idea behind bond formation catalyzed by a receptor as described herein contemplates the use of analog-ligands in the preparation of antibodies of predetermined specificity that preferentially bind to and thereby stabilize the transition state for bond formation upon binding to the specified reactant ligand. The analog-ligands simulate the stereochemical configuration of a high energy transition state in bond formation to induce the production of antibodies having the ability to bind to a reactant ligand when that ligand is in the appropriate stereochemical configuration, and to catalyze bond formation in the bound reactant ligand. Following the terminology of enzymology, the reactant ligand can also be referred to as a ligand, substrate, a substrate ligand or a reactant ligand substrate.

Such preferential binding and stabilization results in a reduction in the activation energy for the bond-forming reaction, thus meeting a criterion for catalysis. Antibodies that display this property can be obtained by immunization with synthetic analogs that are chemically modified to resemble the bonding characteristics of a substrate ligand undergoing bond formation; i.e., by immunization with transition state analogs of the particular bond-forming reaction.

The mechanism by which an antibody forms an ester or amide or other bond of a bound ligand can be thought of in terms of an "induced fit" model. As the loosely bound substrate distorts or rearranges to conform to the binding geometry of the antibody combining site, stress can be relieved by chemical reorganization of the atoms involved in bond formation such as an exemplary carbonyl carbon and an amine or alcohol of the ligand such that this reorganization leads to the formation of the desired bond.

The transition state mimicked by the analog-ligand, and therefore bound by the antibody combining site, can stereochemically resemble the reactant, the product or a stereochemical configuration that is between reactant and products along the reaction coordinate. The "reaction coordinate" is, like a transition state, a mental construct used by chemists to describe the progress of a reaction from a mechanistic viewpoint. The transition state is located at a potential energy peak as a reaction progresses. When graphed potential energy is normally the ordinate and the reaction coordinate is the abscissa.

The carboxylic acid ester and amide hydrolytic transition state analogs of Tramontano and Lerner and Pollack et al. discussed earlier resembled a transition state about midway between reactant and product. The work reported in WO 85/02414 did not appear to contemplate mimicking a transition state, but rather reactant, intermediate or product, and in the only concrete example utilized the reactant for the principal immunogen and a product-appearing portion of the reactant linked directly to a carrier for a secondary immunogen.

The work described in detail hereinafter utilized a transition state analog-ligand as immunogen that resembled the desired product; i.e., the arrangement of the bonds of the analog-ligand that are involved in the bond-forming reaction resembled the arrangement of those bonds in the product more than they resembled the starting material or an arrangement about midway between the reactant and product. Thus, the transition state analog-ligand utilized was in the form of a cyclic phosphonate so that the induced receptor molecule would itself induce the acyclic reactant ligand into the cyclic configuration of the product and thereby not only lower the potential energy of activation by binding to the tetrahedral configuration of the carbonyl carbon during bond formation, but also reduce the rotational entropy of the reactant ligand upon the binding of that ligand by the receptor.

Still further, the transition state mimicked the stereoconfiguration of the product so that only those reactant ligand molecules that could form the product of the desired stereoconfiguration could be effectively bound by the receptor synthase. As a consequence, substantially only one of two possible stereoisomers was formed in the catalyzed reaction.

The term "receptor" is used herein to mean a biologically active molecule that binds to a reactant ligand as well as to an analog-ligand. The receptor molecules of the present invention are antibodies, substantially intact antibodies or idiotype-containing polyamide (paratopic) portions of an antibody. Biological activity of a receptor molecule is evidenced by the binding of the receptor to its antigenic reactant ligand or analog-ligand upon their admixture in an aqueous medium, at least at physiological pH values and ionic strengths. Preferably, the receptors also bind to the antigenic reactant ligand or analog-ligand within a pH value range of about 5 to about 9, and at ionic strengths such as that of distilled water to that of about one molar sodium chloride.

Idiotype-containing polyamide portions (paratopes or antibody combining sites) of antibodies are those portions of antibody molecules that include the idiotype, and bind to the reactant ligand or analog-ligand. Such portions include the Fab, Fab' and F(ab')$_2$ fragments prepared from antibodies by well-known enzymatic cleavage techniques. See for example, U.S. Pat. No. 4,342,566 to Theofilopoulos and Dixon, generally, and specifically, Pollack et al., *Science,* 234, 1570 (1987), who reported accelerated hydrolytic rates for Fab fragments were the same as those of the native Ig. Inasmuch as the antibodies from which idiotype-containing polyamides are obtained are described as raised against or induced by immunogens, idiotype-containing polyamide receptors are also discussed as being "raised" or "induced" with the understanding that a cleavage step is usually required to obtain an idiotype-containing polyamide from an antibody. Intact antibodies are preferred, however, and are utilized herein as illustrative of the receptor molecules of this invention.

The receptors useful in the present invention are more preferably monoclonal antibodies. A "monoclonal antibody" is a receptor produced by clones of a single cell called a hybridoma that secretes but one kind of receptor molecule that binds to a reactant ligand or analog-ligand. The hybridoma cell is fused from an antibody-producing cell and a myeloma cell or other self-perpetuating cell line.

Techniques for preparing the monoclonal antibodies of the present invention are well known. Such receptors were first described by Kohler and Milstein, *Nature,* 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

Monoclonal receptors are preferred herein because of their unique specificity in binding to a single epitope such as a particular stereoisomer of the immunizing analog-ligand and reactant ligand, as well as their relatively higher specific catalytic activities as compared to polyclonal antibodies. Polyclonal antibody preparations can also be used herein, but typically have to be separated into fractions that bind to and catalyze a desired stereoisomer and those that bind to the non-desired stereoiosomer.

Antibodies that bind to desired and non-desired stereoisomers can be separated by affinity separation using an analog-ligand having the desired or non-desired stereoisomer as the affinity sorbant. After admixture and maintenance of an antibody preparation with the affinity sorbant for a time sufficient for appropriate immunoreaction to take place, the affinity sorbant is separated from the remaining portion of the antibody preparation.

The separated, remaining antibody portion contains the antibodies that bind to the desired stereoisomer where the non-desired stereoisomer is used as the affinity sorbant. On the other hand, where the desired stereoisomer is used as the affinity sorbant, the separated, remaining antibody portion contains antibodies that bind to the non-desired stereoisomer, whereas the antibodies that bind to the desired stereoisomer are bound to the affinity sorbant. Those latter antibodies can thereafter be isolated by usual techniques for separating bound entitites from affinity sorbants, such as washing the sorbant with glycine-hydrochloride at pH 2.

In either event, mixed polyclonal antibodies that bind to a desired configuration can be obtained. However, those antibody mixtures can contain antibodies that do not catalyze the reaction. As a result, the specific catalytic activity of such a mixed antibody preparation is typically lower than is the specific activity of a monoclonal receptor.

A "ligand" is defined herein as a molecule or complex that immunoreacts with or binds to a receptor molecule antibody combining site. Two types of ligand are contemplated herein. A first is termed an analog-ligand and is used as an immunogen to induce preparation of receptor molecules and as an inhibitor of the receptor molecule synthase-catalyzed reaction. The second is referred to as the ligand, reactant ligand, substrate, substrate ligand or reactant ligand substrate and is the molecule that undergoes the catalyzed reaction. The analog-ligand is substantially inert to undergoing the catalyzed reaction.

As described herein, chemical analogs of ester ligands have been synthesized that incorporate phosphonate moieties at a specific, predetermined site to mimic the atomic configuration of the transition state leading to the formation of an amide or ester bond. Such analogs are suitable candidates for this investigation because it is known that phosphonamidates have been used as transition state analogs in the inhibition of proteolytic enzymes [Bartlett, et. al., *Biochemistry*, 22, 4618 (1983 )].

Short polypeptide chains can induce the production of antibodies that recognize and bind to a homologous protein at a predetermined specific site. The present invention carries the earlier work with polypeptides a major step forward. Here, the antibodies (receptors) are induced by an immunizing haptenic first molecule (the analog-ligand), and recognize and bind not only to that first molecule, but also to a second, related molecule (the reactant ligand). In binding that second molecule, the receptor causes bond formation (which as demonstrated herein can be catalytic and stereospecific ) of a preselected, ester or amide bond that corresponds in topology to the topology of the immunizing, haptenic first molecule. The correspondence in topology; i.e., size, shape (stereochemical configuration) and charge, provides a means for preselecting the site at which bond formation of the reactant ligand occurs.

Consequently, by synthesis of a relatively small, immunizing haptenic analog-ligand, one can induce the production of receptor molecules that recognize, bind to and catalytically form a bond such as an ester or amide bond in a larger molecule that can contain a plurality of amide or ester bonds. Thus, a receptor can be prepared that causes formation of a selected, predetermined bond in only one stereoisomeric form of a product molecule. The implication of this result is that one can confer the activity of hitherto unknown synthases to immunoglobulins.

Furthermore, for syntheses of amides and esters, the activity of the antibody can be directed to any predetermined site at will by designating the amide or ester bond to be formed with the phosphonamidate or phosphonate configuration in the haptenic analog-ligand used for immunization.

II. Transition State of Bond Formation

Analog-Ligand and Reactant Ligand Design

Design of the analog-ligand flows backward from the structure of the product to be formed through the transition state for bond formation to be mimicked, and then to the analog-ligand. Reactions that involve ring opening or ring closing provide illustrative examples of the general concept and are utilized herein as exemplary for a cyclic amide- or ester-forming (lactam or lactone) reaction.

Amide or ester bond formation reactions catalyzed by an amide or ester synthase of the present invention are in some ways analogous to transacylation processes that are characterized by carbonyl addition-elimination mechanisms. The acyl group may, therefore, possess varying degrees of tetrahedral character in this transition state. W. P. Jencks, *Catalysis in Chemistry and Enzymology*, ch. 10, (McGraw-Hill, New York, 1969). The enzymes that catalyze transacylation reactions might be expected to bind well those analogs of the ligand having a tetrahedral configuration about the acyl center. This is true for serine proteases, where a covalent bond between the ligand and the enzyme is formed temporarily [Westerik et al., *J. Biol. Chem.*, 247, 8195 (1972); R. C. Thompson, *Biochemistry*, 12, 47 (1973) and Imperali et al., *Biochemistry*, 25, 3760 (1986)], as well as for enzymes that catalyze the direct hydration of amides or esters. The latter category is inhibited by compounds with a tetrahedral configuration including a phosphate, phosphonate or phosphonamidate group in lieu of the scissile amide unit [Weaver et al., *J. Mol. Biol.*, 114, 119 (1977) and Jacobsen et al., *J. Am. Chem. Soc.*. 103, 654 (1981)].

Naturally occurring and synthetic substances containing phosphorus have been studied as inhibitors of metallopeptidases. In these enzymes, the transition state would appear to contain the hydrated amide in the coordination sphere of the metal ion [W. N. Lipscomb, *Acc. Chem. Res.*, 15, 232 (1982)]. A complete picture of a transition state analog might then have the phosphono group of an inhibitor as a ligand to a metal ion or some other polarizing site [Weaver et al., *J. Mol. Biol.*, 114, 119 (1977) and Christianson et al., *J. Am. Chem. Soc.*, 108, 545 (1986)]. The role of the metal ions in metallopeptidases, however, is not clearly understood. The metal may have a multiple function in amide hydrolysis where proton transfer steps among the tetrahedral. intermediates may be rate-limiting [L. M. Sayre, *J. Am. Chem. Soc.*, 108, 1632 (1986)].

The formation of a carboxylic amide or ester is a simple example of acylation that can also be approximated by the phosphonate-containing analog of the tetrahedral transition state. The binding of the phosphonate group may describe a stabilizing interaction in the transition state which would lead to catalysis. Amide and ester formation reactions generally do not proceed at convenient spontaneous rates under ambient conditions that are suitable for antibodies. Therefore, bond formation (or loss of substrate) can be readily detected.

The structures of the analog-ligands and ligands for this investigation were selected according to certain criteria. These included the availability and stability of the organophosphorus precursors, the corresponding carboxylic acid substrate, the convenience of the chemical synthesis for its preparation, and the adaptability to diverse schemes for immunological presentation.

An exemplary basic molecular unit for the analog-ligand that provides the structural features necessary for inducing production of a lactone synthase is the phosphorus-containing cyclic compound of formula III that is shown below:

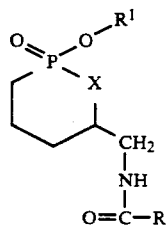

wherein
X is O or NH;
R is selected from the group consisting of hydrogen, $C_1$-$C_6$ lower alkyl and a linking group alone or bonded to an antigenic carrier; and
$R^1$ is selected from the group consisting of hydrogen $C_1$-$C_6$ lower alkyl, benzyl and phenyl.

As is apparent from the above formula, when X is an oxygen atom (0), the analog-ligand is a lactone (cyclic phosphonate), whereas when X is a nitrogen atom bonded to a hydrogen atom (NH) the analog-ligand is a lactam (cyclic phosphonamidate).

An analog-ligand of the above formula can be linked to an antigenic carrier molecule through an appropriate linking group R. Specific linking groups and antigenic carrier molecules are discussed hereinafter.

A particularly preferred analog-ligand has a structure represented by formula II, below:

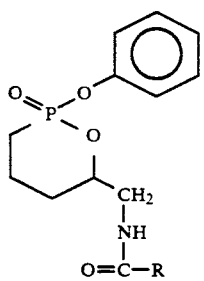

wherein R is selected from the group consisting of hydrogen, $C_1$-$C_6$ lower alkyl, and a linking group alone or bonded to an antigenic carrier molecule.

When used as an immunogen, the R group of the haptenic analog-ligand is preferably a linking group bonded to an antigenic carrier, as described hereinafter. When used as an inhibitor, as in the studies shown in FIG. 2, the R group is preferably methyl ($C_1$ alkyl).

Examination of the structures of the analog-ligands of formulas III and II reveals that there are two centers of chirality, at the phosphorus atom and at the carbon atom adjacent to the X and 0 of the formulas, respectively; i.e., the alpha-carbon of the alcohol or amine portions of the ester or amide. Thus, the analog-ligands depicted can exist as a total of four stereoisomers (diastereomers); i.e., two pairs of enantiomers. Further pairs of enantiomers are possible where $R^1$ and R contain chiral centers. Data from nuclear magnetic resonance spectroscopy indicated that the ring closure reaction that formed the primary amine corresponding to formula II was stereospecific as to the phosphorus atom, and only one diastereomer (a single pair of enantiomers) was in fact formed.

The reactant ligand (substrate) structurally capable of forming an amide or ester bond and that contains a carbonyl group carbon atom and an amine or alcohol group can be a single molecule that contains both of the reactive functionalities, or those functionalities (carbonyl carbon and amine or alcohol) can be on separate molecules. The singular form of the word "ligand" is utilized for both the single and two molecule species since once bound, either type of those entities behaves as a single molecule.

A preferred reactant ligand capable of forming a lactam or a lactone corresponding to the analog-ligand of formula III has a structure of formula IV, below:

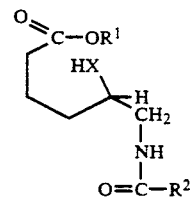

wherein X and $R^1$ are as before-described, and $R^2$ is hydrogen for $C_1$-$C_6$ lower alkyl, preferably methyl ($C_1$).

A particularly preferred ligand of formula IV is the ligand that has the structure of formula I, below:

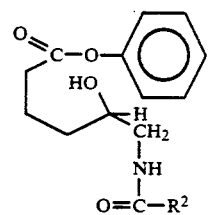

wherein $R^2$ is as described before.

It is noted that the reactant ligands of formulas IV and I also contain a chiral carbon atom. Again, that chiral atom is the carbon bonded directly to the amino or hydroxyl group of the amine or alcohol portion of the amide or ester to be formed; i.e., the alpha-carbon. In view of the chirality of that atom, the reactant ligand substrates depicted in formulas IV and I normally exist as a racemic modification of two enantiomers. Further enantiomers (diastereomers) can also exist for those formulas, depending on the structures of $R^1$ and $R^2$ as noted previously.

The structures depicted in formulas IV and I depict the four different groups bonded to the chiral atom, whereas the structures of formulas III and II omit the hydrogen atom (H) bonded to that atom for improved clarity in viewing the formulas. All four of those formulas omit the hydrogen atoms between the phosphorus atom or carbonyl carbon atom and the chiral atom for the same reason. The individual carbon atoms bonded to those omitted hydrogens and the chiral carbon itself are shown as the vertices of the lines joining the phosphorus atom or carbonyl carbon following procedures for depicting such atoms as is customary in organic chemistry.

An antibody molecule and its combining site are chiral, being a polymer of naturally occurring optically active L-amino acid residues. Because of the particular make-up of amino acid residues of the binding site and the folding of those residues, an antibody combining site can also preferably bind to one of two stereoisomers. This fact is shown herein by the preferential binding and reaction with one of a pair of enantiomers as compared to the other. The present invention makes use of the exquisite binding properties of antibody combining sites to catalyze the synthesis of one stereoiosmeric product, here an enantiomer, as compared to the other stereoisomeric product that might otherwise also be formed by the catalytic reaction.

Thus, one aspect of the present invention contemplates a method for carrying out a stereoselective synthesis to prepare a preselected product containing relatively more of one stereoisomer than another stereoisomer that might be formed. In carrying out the synthesis, a reactant ligand structually capable of forming the product and an effective amount of a synthase molecule are admixed in an aqueous medium to form a reaction mixture.

The reaction mixture so formed is maintained for a time period sufficient for the stereoisomeric product to form, e.g. minutes to days. The desired stereoisomeric product is thereafter typically recovered from the remainder of the reaction mixture.

That remaining reaction admixture can also include the synthase, unreacted reactant ligand of the desired stereoconfiguration (where the reaction has not gone to completion), unreacted reactant ligand of the non-desired stereoconfiguration (where a mixture such as racemic modification of two enantiomeric reactant ligands is used), and product of the non-desired stereoconfiguration (where an uncatalyzed reaction takes place or where complete stereospecific catalysis is not obtained). The desired product need not be recovered in instances where it is to be used as present in the reaction mixture, such as where a subsequent reaction is to be performed.

The reactant ligand utilized is capable of forming at least two stereoisomers of the product; i.e., cis/trans isomers or enantiomers. It is to be understood that more than two stereoisomers such as diastereomers can be formed in several reactions contemplated herein. When more than one pair of stereoisomers can be formed, at least one of the stereoisomers is formed in preference to the others. Where diastereomers are involved, the at least one preferentially formed stereoiosomer can include a pair of enantiomers.

The synthase molecule comprises a receptor molecule, preferably monoclonal, that contains an antibody combining site capable of stereospecifically catalyzing the formation of the product. That combining site binds to: (a) substantially only one stereoisomer of the reactant ligand and (b) a ligand structurally analogous to a transition state that leads to one stereoisomer of the product; i.e., the analog-ligand.

Useful synthase molecules are prepared by immunizing an animal such as a mouse with an analog-ligand as immunogen to induce production of antibodies to the analog-ligand. The presence of antibodies that bind to the analog-ligand can be determined by a simple screening procedure such as the enzyme-linked immunosorbant assay (ELISA) described herein. Once a positive binding result is obtained for a polyclonal antibody preparation, an antibody preparation that binds preferentially to the desired stereoisomer can be obtained by a method described before.

Where a monoclonal synthase is desired, a polyclonal antibody preparation can be screened for general binding reactivity with the analog-ligand, and hybridomas thereafter prepared by standard techniques from a myeloma line and appropriate cells of the animal used to prepare the positive-binding antibody preparation. Since the monoclonal antibodies secreted by the prepared hybridomas should also be screened for immunoreaction with the analog-ligand, the first screening of polyclonal antibodies is not always necessary.

Thus, the monoclonal antibodies secreted by the produced hybrioma are typically screened first for those that bind to a desired stereoisomer of the analog-ligand, and thereafter the antibodies that bind are screened for the capacity to catalyze the desired reaction of the reactant ligand. Since the desired result is catalysis of a particular stereoselective reaction, the screening for binding to an analog-ligand of the desired stereochemistry can also be omitted, and the hybridoma secretions screened only for the ability to stereospecifically catalyze the reaction.

The hybridoma(s) that secrete a useful monoclonal antibody is (are) thereafter grown further to produce more of a useful antibody.

In preferred practice, the preselected stereoisomeric product is a pair of enantiomers. In a particularly preferred practice, the synthase molecule is a carboyxlic acid amide or ester synthase.

A method of forming a preselected enantiomeric carboxylic acid amide or ester product that contains an excess of one enantiomer over the other enantiomer is also contemplated herein. Here, an enantiomeric reactant ligand pair structurally capable of forming the enantiomeric product; i.e., a reactant ligand racemic modification, is admixed with an effective amount of a carboxylic acid amide or ester synthase in an aqueous medium to form a reaction mixture.

The reactant ligand contains a carbonyl group carbon atom and an amine or alcohol group structurally capable of forming the preselected carboxylic acid amide or ester product. As noted earlier, the reactive groups, here a carbonyl group and an amine or alcohol group can be in the same molecule as described in detail herein, or in separate molecules as where the carbonyl group carbon atom is in a compound such as that of formula II where R is methyl and the amino nitrogen is that of aniline, for example, that is admixed to form an anilide by a catalyzed reaction. Aside from a doubly bonded oxygen atom, the carbonyl carbon atom is typically singly bonded to an alpha-carbon atom and singly bonded to another, leaving, group atom such as the oxygen of the alcoholic portion of an ester, the nitrogen of the amine portion of an amide, a halide, the nitrogen of an azide group or the sulfur of a thiolester. The reactant ligand can thus be referred to as containing a carbonyl group that is activated toward amide or ester formation as compared to the carbonyl group of a carboxylic acid.

The amide or ester synthase molecule comprises a receptor molecule, preferably monoclonal, that contains an antibody combining site capable of catalyzing the formation of the preselected enantiomeric amide or ester product. That combining site binds to: (a) substantially only one enantiomer of the enantiomeric ligand pair, and (b) a ligand structurally analogous to one enantiomer of a transition state leading to the preselected amide or ester product; i.e., the analog-ligand.

The enantiomer of the analog-ligand that is bound by the combining site contains a tetrahedrally bonded phosphorus atom that is located at the position occupied by the carbonyl group carbon atom of the carboxylic acid amide or ester product. That tetrahedrally bonded phosphorus atom is itself bonded directly to: (i) the alpha-carbon of the acid portion of the analog-ligand by a single bond; (ii) a first oxygen atom that is doubly bonded to the phosphorus atom; (iii) a second oxygen atom that is singly bonded to the phosphorus atom, and is singly bonded to a radical selected from the group consisting of hydrogen, $C_1$-$C_6$ lower alkyl, benzyl and phenyl; and (iv) a third oxygen atom or a nitrogen atom that is singly bonded to the phosphorus atom, and is also singly bonded to the alpha-carbon of the amine or alcohol portion of the analog-ligand. It is to be understood that the nitrogen atom can be of a primary amine or an appropriately substituted secondary amine. This is true for all of the amine portions discussed herein, although the preferred exemplary analog-ligand and reactant ligands of formulas III and IV, respectively, are shown as primary amines. Tertiary amines do not form amides.

For formation of a cyclic amide or ester as is prepared illustratively herein, there are not distinct acid and amine or alcohol portions of the molecule. However, those skilled in organic chemistry will understand that amides and esters must by definition contain acid and amine or alcohol portions. Thus, an imaginary line of demarcation can be drawn for such molecules that includes at least the carbonyl carbon and its directly bonded alpha-carbon in the acid portion of the molecule and includes the amino or hydroxyl group and its directly bonded alpha-carbon in the amine or hydroxyl portion of the molecule.

The reaction mixture so formed is maintained for a time period sufficient for the preselected carboxylic acid amide or ester product enantiomer to form, as already noted. That product is again preferably recovered, although such recovery is not required.

Preferably, the amide or ester synthase is a lactam or lactone synthase. This synthase is also preferably an intact antibody. Most preferably, the ester or amide synthase is secreted by hybridoma 24B11 that was deposited with the American Type Culture Collection (ATCC) of Rockville, Md., pursuant to the Budapest Treaty on Aug. 4, 1987 and bears the accession number HB9488.

A method of forming a preselected carboxylic acid amide or ester product is also contemplated. In accordance with this method, a reactant ligand structurally capable of forming the amide or ester product is admixed with an effective amount of an amide or ester synthase in an aqueous medium to form a reaction mixture.

The reactant ligand contains a carbonyl group carbon atom and an amine or alcohol group structurally capable of forming the preselected carboxylic acid amide or ester. The carbonyl carbon atom is bonded to an oxygen atom, an alpha-carbon atom and an atom of a leaving group as previously described for the reactant ligand for synthesis of an enantiomeric ester or amide.

The amide or ester synthase molecule comprises a receptor molecule, preferably monoclonal, that contains an antibody combining site capable of catalyzing the formation of the preselected amide or ester product. That combining site binds to the reactant ligand and also to a ligand structurally analogous to the preselected amide or ester product; the analog-ligand.

The analog-ligand contains a tetrahedrally bonded phosphorus atom located at the position of the carbon atom of the carbonyl group of the preselected carboxylic acid amide or ester product. That tetrahedrally bonded phosphorus atom is bonded directly to: (i) the alpha-carbon of the acid portion of the analog-ligand by a single bond; (ii) a first oxygen atom that is doubly bonded to the phosphorus by a single bond; (iii) a second oxygen atom that is singly bonded to the phosphorus atom and is singly bonded to a radical selected from the group consisting of hydrogen, $C_1$-$C_6$ lower alkyl, benzyl and phenyl; and (iv) a third oxygen atom or a nitrogen atom that is singly bonded to said phosphorus atom, and is also singly bonded to the alpha-carbon of the alcohol or amine portion of the analog-ligand.

The reaction mixture is maintained for a time period sufficient to form the preselected amide or ester product, as already noted. That product can thereafter be recovered, as discussed previously for other products.

The synthase molecule is preferably a lactam or lactone synthase. The synthase can also catalyze the amide or ester bond formation chirally to form relatively more of one of a pair of stereoisomeric products such as enantiomers, than the other of the pair. Thus, an amide or ester synthase useful in a before-described method can also be utilized in this method.

A synthase molecule useful in the method described immediately above or in any of the methods previously described can be an intact antibody, which is preferred, or a smaller, antibody combining site-(paratope-) containing portion of an antibody such as Fab or Fab' portion of an antibody.

Each of the previously described synthetic methods utilizes an aqueous medium as a portion of the reaction admixture. That medium typically contains water and buffer salts. In addition, the medium can contain other salts such as sodium choride, as well as water-soluble calcium and magnesium salts as are frequently found in protein-containing media. Other water-soluble polyvalent metal salts such as iron and cobalt salts can also be present and are useful complexing agents where the reactant ligand is comprised of two separate molecules. Organic solvents such as methanol, ethanol, acetonitrile, dimethyl sulfoxide, dioxane, hexamethylphosphoramide and N,N-dimethylforamide can also be present. Surface active agents that emulsify the reactant ligand and synthase molecule can also be present. The critical feature of ingredients present in the aqueous medium is that those ingredients not substantially interfere with or inhibit the catalytic reaction as by denaturation of the synthase molecule. Additionally, the aqueous medium is substantially free from salt, proteins generally, and enzymes, specifically, that inhibit the bond-forming reaction catalyzed by the synthase molecule.

The aqueous medium typically has a pH value of about 5 to about 9, and preferably about pH 6.0 to about 8.0. pH values greater and less than those recited values can also be utilized so long as the catalyzed reaction is again not substantially interfered with or inhibited.

The catalytic reactions are typically carried out at ambient room temperature; i.e., at about 20 to about 25 degrees C., and at an ambient atmospheric pressure. However, temperatures down to about the freezing point of the aqueous medium and up to about the boiling point of the medium at atmospheric pressure can also be used. As is known, proteins such as the synthase molecule tend to denature at elevated temperatures such as those at which an aqueous medium boils, e.g. at about 100 degrees C., and thus temperatures below about 40 degrees C. are preferred. As is also well known, reactions that follow multimolecular kinetic expressions decrease in rate as the temperature decreases. Thus, a minimal temperature of about 15 degrees is preferred.

The reactant ligand is present in a reaction mixture in an amount up to its solubility in the aqueous medium. A two phase system that includes insoluble reactant ligand can also be used, but normally is not so used. Normally used concentrations of the reactant ligand are about 0.1 micromolar (uM) to about 10 millimolar (mM), with that amount also being a function of the solubility of the reactant ligand in the solvent medium. Where the product is desired, per se, relatively higher concentrations are used as compared to lower concentrations where a reaction mechanism or reaction kinetics are to be studied.

An effective amount of the synthase molecule is also present. That effective amount is typically a catalytic amount; i.e., the synthase is used at a molar ratio to the reactant ligand of about 1:5 to about 1:10,000. The ratio of synthase molecule to reactant ligand typically depends upon the specific activity of the synthase molecule toward the substrate ligand and the purpose of the user in running the reaction. Thus, where the product is desired, a relatively higher concentration of synthase and higher synthase to reactant ligand ratio are used. Where the reaction mechanism or kinetics of the reaction are being studied, a lower concentration and ratio are typically used. A stoichiometric amount of synthase or less can also be used, but since the synthase is a catalytic molecule, use of even a stoichiometric amount can be wasteful. Thus, at least a catalytic amount of the synthase is utilized.

The present invention also contemplates a receptor molecule that exhibits synthase activity and comprises a receptor molecule that is preferably a monoclonal receptor.

In one embodiment, the receptor has an antibody combining site capable of catalyzing stereoselective synthesis and can catalyze the preparation of a preselected product that contains relatively more of one stereoisomer than the other stereoisomer. The antibody binding site binds to: (a) substantially only one stereoisomer of a reactant ligand that is structurally capable of forming the product and also (b) substantially only one steroisomer of an analog-ligand that is structurally analogous to a transition state leading to one stereoisomer of the product.

As noted earlier, steroisomers can be geometric isomers or optical isomers. In the reactions discussed in detail hereinafter, the reactant ligand used was an enantiomeric pair that reacted to form substantially only one of the possible enantiomeric products in the catalyzed reaction. The analog-ligand used to induce production of the monoclonal synthase receptor molecule was itself one of a pair of diastereomers; i.e., an enantiomeric (optical isomer) pair of geometric isomers in which the phenoxy group of the phosphonate group could be in a 1,3-cis or -trans relation to the aminomethyl group.

A useful synthase molecule can thus selectivey catalyze a reaction that preferentially leads to formation of one cis or trans isomer over the other. Similarly, a useful synthase molecule can selectively catalyze a reaction that preferentially leads to the formation of one enantiomer over the other enantiomer.

As already noted, a synthase molecule that contains an antibody combining site capable of catalyzing the formation of a preselected enantiomer of a carboyxlic acid amide or ester product is also contemplated herein. That antibody combining site binds to substantially only one enantiomer of an enantiomeric reactant ligand pair, and to a ligand structurally analogous to one enantiomer of a transition state leading the preselected amide or ester product. The enantiomer of the analog-ligand that is bound by the combining site has a tetrahedrally bonded phosphorus atom located at the position occupied by the carbon atom of the carbonyl group of the carboxylic acid amide or ester product. The other atoms bonded to that phosphorus and the number of bonds between each of those atoms and the phosphorus atom are as previously described.

It is to be noted that the stereoconfiguration of the reactant molecule need not be that of the product that is formed preferentially, whether that product is an optical or geometric isomer. The stereoconfiguration of the reactant ligand and that of the analog-ligand also need not be the same. Rather, the stereoconfiguration relationship between the reactant ligand, analog-ligand and product is a function of the particular reaction that is being catalyzed.

More specifically, where an atom involved in the bond-forming reaction itself has a particular stereoconfiguration and the catalyzed reaction involves a displacement such as a nucleophilic displacement that proceeds by an $S_n2$ mechanism, the stereoconfiguration at that atom inverts to the opposite configuration. When such an atom is also a chiral center, the reactant ligand possesses a first stereoconfiguration whereas an analog-ligand that resembles a product-like transition state has a second, inverted stereoconfiguration of the product.

On the other hand, where the atom at which bond formation takes place does not possess two stereoconfigurations or where an inversion of configuration is not involved in the bond-forming reaction, the stereoconfiguration of the reactant ligand, analog-ligand and product are substantially the same.

This is the case for the lactone formation described in detail herein since the carbonyl carbon of the ester reactant ligand of formula I, while involved in the bond-forming reaction, does not exist in two stereoconfigurations, whereas the alpha-carbon of the alcohol portion of that ligand has d and l isomeric forms, but no inversion or other stereochemical change is involved at that carbon. The phosphonate group of the analog-ligand of formula II can exist in two stereochemical forms, as can the alpha-carbon of the alcohol portion of the cyclic phosphonate. However, as noted herein, only one of the phosphonate diastereomers formed when that analog-ligand was prepared. Thus, the remaining center of stereoisomerism, the alpha-carbon of the alcohol portion of the cyclic phosphonate, had the same stereoisomeric forms as the analogous alpha-carbon of the reactant ligand alcohol portion.

The present invention still further contemplates a molecule exhibiting amide or ester synthase activity that comprises a receptor molecule. The preferably monoclonal receptor contains an antibody combining site capable of catalyzing the formation of a preselected carboxylic amide or ester bond. The combining site binds to: (a) a ligand containing a carbonyl carbon atom and an amine or alcohol group that are structurally capable of forming the preselected carboxylic amide or ester bond; and (b) a ligand structurally analogous to the preselected amide or ester; the analog-ligand having a tetrahedrally bonded phosphorus atom located at the position occupied by the above-mentioned carbonyl carbon atom of the preselected carboxylic amide or ester bond of the before-mentioned ligand. The tetrahedrally bonded phosphorus atom is itself directly bonded to: (i) the alpha-carbon atom of the acid portion of the ligand by a single bond; (ii) a first oxygen atom that is doubly bonded to the phosphorus atom; (iii) a second oxygen atom that is bonded to the phosphorus atom by a single bond, and is singly bonded to a radical selected from the group consisting of hydrogen, $C_1$–$C_6$ lower alkyl, benzyl and phenyl; and (iv) a third oxygen atom or a nitrogen atom singly bonded to the phosphorus atom, and is also singly bonded to the alpha-carbon atom of the amine or alcohol portion of the ligand.

In preferred practice, the molecule exhibits lactone synthase activity. Thus, the ligand containing the carbonyl carbon is capable of forming a lactone, and the analog-ligand is a cyclic phosphonate, as exemplified by 2-phenoxy-2-oxo-6-(acetamidomethyl)-1,2-oxaphosphorinane.

The phrase "structurally capable of forming a preselected carboxylic amide or ester bond" and similar phrases using the words "structurally capable" are utilized herein to indicate that the structure of the ligand is such that it will permit and not inhibit, as by steric hinderance or by the absence of necessary reactive groups, the bond to be formed.

III. Coupling of Compounds to Protein Carriers

Conjugates of haptenic analog-ligand molecules with protein carriers such as keyhole limpet hemocyanin (KLH) can be prepared, for example, by activation of the carrier with a linking agent such as MBS (m-maleimidobenzoyl-N-hydroxy succinimide ester), and coupling to the thiol group of the analog-ligand. See, for example, Liu et al., *Biochem.*, 80, 690 (1979). As is also well known in the art, it is often beneficial to bind a hapten to its carrier by means of a linking group that is reacted first with the hapten and then the resulting hapten/linker is reacted with the antigenic carrier. Thus, the hapten is activated rather than the carrier. The acyl chloride portion of these linkers typically reacts first.

In addition to MBS, glutaraldehyde and other well known linking groups, two other linking groups have been found useful. These linkers are N-hydroxysuccinimidyl glutaryl chloride and N-hydroxysuccinimidyl adipoyl chloride whose syntheses are described herein.

Useful antigenic carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as poly-amino acids such as poly(D-lysine:D-glutamic acid), and the like.

The choice of carrier is more dependent upon the ultimate intended use of the antigen or immunogen than upon the determinant portion of the antigen, and is based upon criteria not particularly involved in the present invention. For example, a carrier that does not generate an untoward reaction in the particular laboratory utilized animal should be selected.

The exemplary immunogenic conjugate was prepared from the cyclic phosphonate by adapting its synthesis to incorporate a straight chain of carbon atoms on the methylene amino group of the lactone as a spacing element. It was concluded that the flexible carbon chain of an glutarate appendage would reduce any bias to immunoreactivity due to the conformational constraint imposed by covalent attachment to the carrier protein. The bifunctional reagent prepared for this purpose also delivers the preactivated carboxyl group for linkage via amide bond formation with the lysine residues of the carrier. The particular coupling method used in this study is further described herein. The cyclic phosphonate was coupled to keyhole limpet hemocyanin (KLH) through a methylene amino group.

According to the present invention, the intermediate linking agent is preferably succinimidyl glutaryl chloride that was prepared as described hereinafter.

IV. Separation of Stereoisomers

The present invention also provides a method of separating stereoisomers from each other. Here, a mixture of stereoisomers and a receptor molecule containing an antibody combining site that immunoreacts with substantially only one of those stereoisomers are admixed in an aqueous medium to form an admixture. The admixture is maintained for a time period sufficient for the receptor to bind to one of the steroisomers and to form an immunoreactant of the receptor and one stereoisomer within the admixure, and a remaining admixture. The immunoreactant is thereafter separated from the remaining admixture. In preferred practice, the bound stereoisomer is separated from the receptor of the immunoreactant.

In keeping with the preceding discussion, the stereoisomers can be geometric, cis/trans, isomers or optical, enantiomeric isomers. Similarly, the aqueous medium utilized for separation can be an aqueous medium as is used for a carrying out a before-discussed reaction. The concentrations and ratio of receptor and stereoisomers can be as described previously, although a stoicheometric ratio and relatively dilute concentrations are preferred.

Where separations such as those discussed above are carried out, it is preferred to link the receptor molecule to a water-insoluble solid phase matrix to form a solid phase sorbant. Such solid phase sorbants are known in the art as affinity sorbants, and their methods of preparation are well known.

Every material has at least some water-solubility. As a consequence, the term "water-insoluble" is used herein in its usual sense to mean that the matrix and sorbant made therefrom are recovered substantially intact and in substantially the same amount as admixed with the aqueous medium when the separation is carried out. The matrix and sorbant are typically swellable in water, and can form a gel-like solid phase and still be within the purview of a water-insoluble material as contemplated herein.

A particularly preferred affinity sorbant contains a before-described receptor linked to a particulate water-insoluble matrix comprised of cross-linked agarose. Particularly preferred is a cross-linked agarose such as cyanogen bromide-activated Sepharose 4B-CL (Pharmacia Fine Chemicals, Piscataway, NJ) which is readily linked to amine-containing materials such as receptors to form the solid phase sorbant.

Sepharose 4B-CL is utilized herein as an exemplary solid phase matrix. However, additional particulate and monolithic solid phase matrices are also useful herein. Exemplary of such matrices are Sepharose 6B and 4B, glass beads, and the inner and outer surfaces of hollow fibers as are useful in hemodialysis or ultrafiltration. In addition to matrices specifically mentioned herein, several suitable particulate (beaded) matrices are listed in the 1984 Sigma Chemical Company catalogue at pages 98 to 113. Typically, any water-insoluble solid phase matrix that reacts with an amino group or a carboxy group is suitable.

Methods of affixing a receptor molecule to the matrix are also well known by skilled artisans and need not be dealt with in detail herein. Illustratively, however, such methods include use of activated carboxyl groups as are provided by cyanogen bromide treatment of glucose-containing solids and chemical reactions using water-soluble carbodiimide technology, glutaraldehyde linking and the like.

In addition, U.S. Pat. No. 4,357,311 to Schutt discloses a method for preparing an activated microporous substrate to which an antibody can be covalently bonded through trichloro-triazine to yield an activated substrate. That method can also be used herein. Further, numerous methods for immobilizing enzymes that are applicable for affixing a receptor to a matrix are discussed in *Enzyme Technology*, published by Noyes Data Corporation (1983) at pages 38 to 59.

Where the desired stereoisomer is the material bound by the receptor, the immunoreactant formed of the receptor and stereoisomer is first separated from the remaining admixture. Thereafter the bound stereoisomer is separated from the receptor using well known techniques, and typically recovered. Where the desired stereoisomer is not the isomer bound by the receptor, separation of the immunoreactant from the remainder of the admixture provides an aqueous composition containing an enriched amount, and preferably only, the desired stereoisomer.

Precipitation and centrifugation techniques well known in immunochemistry are also useful for separating the immunoreactant from the remaining admixture. These techniques are useful with a solid phase sorbant and also where the admixture is substantially homogeneous.

A wide variety of steroisometric materials can be separated by a method of this invention. So long as the steroisomers can be dissolved in the aqueous medium and the receptor molecule can immunoreact with whichever isomer it preferentially reacts with under the conditions in which the steroisomers are dissolved in the aqueous medium, the isomers can be separated. Successive separations in which the stereoisomers are separated and the separation steps are repeated can be utilized to improve the stereoisomeric purity of separated isomers.

Exemplary stereoisomers that can be separated include relatively small molecules such as the analog-ligand enantiomers and lactone enantiomers discussed herein. Synthetic natural product analogs, agonists and antagonists such as prostaglandin derivatives, terpenes, drugs such as thalidomide, gluethimide, nalorphine, digoxin and other steroidal compounds can be separated by this method. Still further, a polypeptide that contains a D-amino acid residue can be separated from a polypeptide containing the same sequence having an L-amino acid replacement for that D-amino acid residue.

The receptor molecules utilized in this method are preferably monoclonal, for the reasons discussed previously. A synthase molecule as herein described can also be used where appropriate; i.e., where the stereoisomers of the analog-ligand or product are desired, but generally not where stereisomers of the reactant ligand are to be isolated.

Thus, the receptor utilized for this method need not, and preferably does not, catalyze a reaction of either stereoisomer. Rather, it need only preferentially bind to one stereoisomer over the other. Such receptor molecules are relatively easy to prepare.

For example, where the desired isomer to be separated is a synthetic form of a naturally occurring compound such as progesterone, the naturally occurring compound, which exists in nature as one of several possible stereoisomers, is used as the immunogen, and is typically linked to an antigenic carrier molecule such as keyhole limpet hemocyanin (KLH), as by reaction through the progesterone 17-keto group. After immunization to induce production of anti-progesterone antibodies, polyclonal antibodies that immunoreact with the immunogen can be separated from the remaining antibody preparation by usual affinity chromatographic techniques.

After separation of the bound anti-progesterone antibodies from the immunosorbant, those antibodies can be reacted with a second affinity sorbant, and the bound and unbound antibodies separated. The separated antibodies that bound to the first sorbant but not to the second are therefore specific for the stereoconfiguation of the immunogen, whereas those that bound to the second affinity sorbant bind to both stereoisomers. The antibodies specific for the stereoconfiguration of the immunogen can thereafter be used to separate the stereoisomers as described before.

A somewhat less specific antibody preparation can also be prepared by screening only against the molecule of the stereoconfiguration other than that of the immunogen as with an affinity column. Here, the unbound antibodies immunoreact with the molecule of the desired stereoconfiguration or with an extraneous molecule such as the carrier. That antibody preparation can, nevertheless, be used to separate the stereoisomers.

In another procedure, a mixture of the stereoisomers is used as the immunogen, and the resulting antibodies are screened and separated based on their ability to bind to one or both isomers.

Monoclonal receptors useful in this method are readily prepared as described before, using a molecule of the desired stereoconfiguration, its stereoisomer or a mixture of stereoisomers as immunogen, generally as a conjugate to an antigenic carrier. Once secreting hybridomas are formed, one or more useful hybridomas and their monoclonal receptors can be obtained by separately screening the secreted monoclonal antibodies against each of the stereoisomers as in an ELISA, and selecting for use a hybrioma that secretes receptor molecules that immunoreact with substantially only one of the stereoisomers and not with the other stereoisomer. The useful hybridoma is thereafter typically cloned, injected into the peritoneal cavity of an appropriate animal such as a mouse, where the hybridoma was from compatible mouse cells, and the useful monoclonal receptor, as an intact antibody, recovered from the ascites fluid produced.

The present invention is further illustrated by the examples that follow, which are not intended to be limiting.

Example 1: Preparation of Succinimidyl Adipoyl Chloride (Linking Agent)

A solution of adipic acid monomethyl ester (5.4 g, 33.3 mmol) in thionyl chloride (15 ml) was heated at 40 degrees C. for 2 hours. The mixture was then concentrated and distilled in vacuo (boiling point 119 degrees C. at 20 mm Hg) to provide 3.58 g (60 percent yield by weight) of the acid chloride methyl ester. This was dissolved in 20 ml of dichloromethane and N-hydroxysuccinimide (2.75 g, 24.0 mmol) was added, followed by triethylamine (4.2 ml, 30 mmol). The mixture stirred for 10 minutes then diluted with ethyl acetate and washed with 0.5 M HCl and brine. The solution was dried over anhydrous magnesium sulfate, filtered and concentrated to give 4.5 g (87.5 percent yield by weight) of methyl succinimidyl adipate as a colorless oil.

Proton NMR (in CDCl$_3$) delta 3.73 (singlet, 3H); delta 2.90 (singlet 4H), delta 2.70 (multiplet, 2H), delta 2.37 (multiplet, 2H), and delta 1.79 (multiplet 4H).

A solution of methyl succinimidyl adipate (4.5 g, 17.5 mmol), chlorotrimethylsilane (11.1 ml, 87.5 mmol) and sodium iodide (13.1 g, 87.5 mmol) in 10 ml of acetonitrile was heated at reflux for 12 hours. The mixture was then cooled to room temperature and diluted with ethyl acetate. The reaction mixture was washed repeatedly with 5 percent aqueous sodium bisulfite until the organic solution was colorless. Then it was washed with brine, dried over anhydrous magnesium sulfate, filtered and concentrated to provide 3.2 g (71 percent yield by weight) of adipic acid monosuccinimidyl ester as a white solid.

Proton NMR (in CDCl$_3$) delta 3.90 (singlet, 4H), delta 2.70 (multiplet, 2H), delta 2.4 (multiplet, 2H), delta 1.80 (multiplet, 4H).

A mixture of adipic acid succinimidyl ester (1.00 g, 3.80 mmol) and thionyl chloride (5 ml) was heated at 40 degrees C. for 3 hours, then cooled to room temperature and concentrated in vacuo. The residue was stirred several times with dry hexane, the oil was separated and dried in vacuo to provide 0.97 g (90 percent yield by weight) of succinimidyl adipoyl chloride. This was dissolved in dry tetrahydrofuran to make a 5 molar solution, which was used as such in the preparation of compounds suitable for coupling to protein carriers.

Proton NMR (in CDCl$_3$): delta 3.00 (multiplet, 2H), delta 2.90 (singlet, 4H), delta 2.70 (multiplet, 2H), delta 1.80 (multiplet 4H).

Example 2: N-Hydroxysuccinimidyl glutaryl chloride (Linking Agent)

One mole of glutaric anhydride and one mole of N-hydroxysuccinimide were treated in dichloromethane with 1.2 equivalents of triethylamine. This reaction was stirred for 40 minutes, acidified by the addition of 0.5 N hydrochloric acid (HCl) (aqueous), and then extracted with ethyl acetate to form mono N-hydroxysuccinimide glutarate. This glutarate was then combined with 5 moles of thionyl chloride and stirred at room temperature for three hours. The resulting reaction mixture was dried to remove volatiles, and thereby form N-hydroxysuccinimidyl glutaryl chloride.

Example 3:
2-Phenoxy-2-oxo-6-(aminomethyl)-1,2-oxaphosphorinane

One equivalent of phenylphosphorodichloridite was combined with two equivalents of isopropanol and 2 equivalents of triethylamine, and reacted in diethylether for one hour at room temperature as described by Tolkwith et al., *J. Org. Chem.*, 23, 1682 (1958), to produce diisopropylphenylphosphite in 49 percent yield. Boiling point=117–118 degrees C. at 11 mm Hg.

Three equivalents of this phosphite were mixed with one equivalent of 5-bromo-1-pentene and a catalytic amount of about 0.1 equivalent of sodium iodide, and heated at 170–185 degrees C. for three hours to produce phenyl isopropyl 4-pentenylphosphonate in 80 percent yield after flash colum chromatography on silica. Boiling point=148–150 degrees C. at 1.2 mm Hg.

One equivalent of this phosphonate and 1.8 equivalents of iodine were stirred in chloroform at 10 degrees C. for three-four days as described by Zhao et al., *J. Org. Chem.*, 50, 2136 (1985) to produce 2-phenoxy-2-oxo-6-iodomethyl-1,2-oxaphosphorinane in 61 percent yield. Melting point=127.5–128 degrees C.

A suspension containing two equivalents of sodium azide, one equivalent of the above-prepared iodonated oxaphosphorinane and a catalytic amount of about 0.1 equivalent of tetrabutylammonium bromide in benzene/DMF (1:1) was heated to 60–80 degrees C. for 16 hours to produce 2-phenoxy-2-oxo-6-(azidomethyl)-1,2-oxaphosphorinane in 96 percent yield as a white solid.

A solution of the above azide was prepared in ethanol containing 40 percent by weight of 10 percent palladium on carbon and shaken under 40 pounds per square inch (psi) of hydrogen gas for 20–24 hours at room temperature to produce the corresponding amine that was isolated as a viscous oil in a yield of 84 percent. A solution of the amine was then treated in ether with an excess of pyridinium bisulfate to precipitate the amine derivative by forming a bisulfate salt [2-phenoxy-2-oxo-6-aminomethyl-1,2-oxaphosphorinane bisulfate; Compound A bisulfate].

The salt so obtained was neutralized with 5 percent aqueous sodium bicarbonate, extracted into ethyl acetate, and recovered by evaporation of the solvent. The resulting dried amine (Compound A) was dissolved in dichloromethane and treated first with one equivalent of the N-hydroxysuccinimide (NHS) ester of glutaryl chloride and then with 1.2 equivalents of triethylamine to form the NHS-activated glutaramide.

The synthesis of this compound was itself stereospecific, yielding only one diastereomer (one pair of enantiomers) as revealed by a single $^{31}$P NMR resonance at 27.2 ppm relative to 85% H$_3$PO$_4$. Confirmation that the phenoxy and aminomethyl substituents were in a 1,3-trans orientation (axial-equatorial) was obtained from the X-ray crystal structure of the predecessor iodomethyl derivative.

Protein conjugates with the cyclic phosphonate of formula II wherein R was the described succinimidyl glutaryl chloride (Compound X) were prepared by the addition of 0.250 ml of a solution of the phosphonate in DMF [5 milligrams (mg)/ml] to 0.75 ml of a solution of protein (KLH or BSA, 3.33 mg/ml) in sodium phosphate buffer (pH 7.2, 0.2 M) and stirring gently for one hour at 22 degrees C.

The amine described above (Compound A) was also dissolved in dichloromethane and treated with acetic anhydride and triethylamine to form an acetamide derivative (formula II, where R is methyl) after purification by flash column chromatography on silica in a yield of 28 percent as a glass. This derivative is utilized as an inhibitor.

Example 4:
Phenyl-6-acetamido-5-trimethylsilyloxyhexanoate

One equivalent of mono methyl glutarate (Aldrich Chemical Corp., Milwaukee, Wis.) was combined with 1.5 equivalents of thionyl chloride and stirred at room temperature for one hour to form methyl glutarylchloride. Volatile products were removed in vacuo from the resulting compound that was then treated with Cu$^I$CN in acetonitrile at 80 degrees C. for 15 hours as described by Hunig et al., *Angew. Chem. Int. Ed. (Eng)*, 21, 36-49 (1982) (ref. 5), to form an acyl cyanide.

4.7 Grams of the acyl cyanide were shaken in 45 mililiters (ml) of acetic acid and 4.5 ml of acetic anhydride containing 5 percent palladium on carbon (1.12 gm) while under 40 psi of hydrogen gas to form methyl 6-acetamido-5-oxohexanoate as a crystalline solid in 30 percent yield from mono methyl glutarate. The resulting hexanoate was stirred under reflux in 95 percent ethanol containing 1.5 equivalents of potassium hydroxide for 5 minutes to form 6-acetamido-5-oxohexanoic acid. The resulting hexanoic acid was combined with 1.5 equivalents of phenol and stirred with dicyclohexylcarbodiimide (DCC) and dimethylaminopyridine in dichloromethane as described by Hassner et al, *Tet. Lett.*, 1978, 4475–4478 (1978) to form phenyl 6-acetamido-5-oxohexanoate in 26 percent yield as a crystalline solid. The resulting hexanoate was then combined in methanol with three equivalents of sodium cyanoborohydride, and while stirring, the pH value of about 3 was maintained by the addition of a solution of methanolic HCl to form the corresponding alcohol. The alcohol (phenyl 6-acetamido-5-hydroxyhexanoate, formula I where R is methyl) was then converted to the corresponding phenyl 6-acetamido-5-trimethysilyloxyhexanoate, in 96 percent yield as a glassy solid from the above ketone, as described by Sweeley et al., *J. Am. Chem. Soc.*, 85, 2497 (1963) for storage by reaction with trimethylsilylchloride and bis(trimethylsilyl)amine in pyridine for 5 minutes, and was reconverted to the alcohol for use as a substrate ligand by reaction in 0.1 molar citric acid in methanol for 30 seconds at room temperature immediately prior to use.

Example 5: Preparation of Monoclonal Receptors

The foregoing KLH conjugates were immunize mice (129GlX+ strain), and monoclonal antibodies were obtained as described by Niman et al., *Proc. Natl. Acad. Sci. USA*, 77, 4524 (1980) and Niman et al., in *Monoclonal Antibodies and T-Cell Products*, ed., Katz, D. H., 23-51 (CRC Press, Boca Raton, Fla. 1982).

The lymphocytes employed to form the hybridomas of the present invention can be derived from any mammal, such as a primate, rodent (e.g., mouse or rat), rabbit, guinea pig, cow, dog, sheep, pig or the like. As appropriate, the host can be sensitized by injection of the immunogen, in this instance a haptenic analog-ligand, followed by a booster injection, and then isolation of the spleen.

It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3 X 63 Ag8U.1 (ATCC CRL 1597), Y3-Ag1.2.3. (deposited at Collection Nationale de Cultures de Microorganisms, Paris, France, number I-078) and P3X63Ag8 (ATCC TIB 9). The non-secreting murine myeloma line Sp2/0 or Sp2/0-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were female 129GlX+ mice bred in the mouse colony of the Scripps Clinic and Research Foundation, La Jolla, Calif., however, when animals other than mice are used for preparation of the hybridomas, mice or that animal type can be used for the production of ascites fluid.

In particular, exemplary monoclonal receptors were produced by the standard hybridoma technology of Kohler et al., *Nature*, 256, 495 (1975). For the preparation of the exemplary monoclonal receptor designated 24B11, the foregoing immunization protocol was modified as follows. Female 129GlX+ mice were immunized by intraperitoneal injection with an inoculum of conjugate containing 60 micrograms (ug) of Compound X bound to 125 micrograms of KLH in 500 microliters (ul) of emulsion comprised of a 1:1 mixture of phosphate buffered saline (PBS) pH 7.4 and complete Freund's adjuvant. Two weeks later, the mice were again injected in a like manner with an innoculum containing one half the amount of original conjugate in 500 microliters of a solution of a 1:1 mixture of PBS (pH 7.4) and 10 mg/ml alum. After an additional four weeks, the mice were immunized intravenously with one and one-half times the amount of original conjugate in 500 microliters of PBS (pH 7.4). The spleens were removed from the mice 5 days later, and the spleens were fused to myeloma cells.

The spleens cells were pooled and a single cell suspension was made. Nucleated spleen cells ($1.4 \times 10^8$) were then fused with $3 \times 10^7$ Sp2/0 non-secreting myeloma cells in the presence of a cell fusion promoter (polyethylene glycol 2000). The hybridoma that produced a particular monoclonal antibody was selected by seeding the spleen cells in 96-well plates and by growth in Dulbecco's modified Eagle medium (DMEM) containing 4500 mg/liter glucose (10 percent), 10 percent fetal calf serum (FCS), hypoxanthine, aminopterin and thymidine (i.e., HAT medium) which does not support growth of the unfused myeloma cells.

After two to three weeks, the supernatant above the cell clone in each well was sampled and tested by ELISA (enzyme linked immunosorbent assay as described hereafter) for the presence of antibodies against the immunizing analog-ligand. Positive wells were cloned twice by limiting dilution. Those clones that continued to produce analog-ligand-specific antibody after two clonings were expanded to produce larger volumes of supernatant fluid.

Twenty-four secreted monoclonal antibodies were further screened for hydrolytic activity (25 mM phosphate buffer at a pH 7.0, 25 degrees C.) by monitoring substrate depletion using high performance liquid chromatography (HPLC). One hybridoma and its monoclonal antibody, 24B11, were chosen for further study of catalytic activity.

The hybridoma and the monoclonal receptors produced therefrom and described herein are identified by the designation 24B11, the particular material referred to being apparent from the context. Hybridoma 24B11 was deposited on Aug. 4, 1987 at the American Type Culture Collection, Rockville, Md. and were given the ATCC accession number HB9488.

The present deposits were made in compliance with the Budapest Treaty requirements that the duration of the deposits should be for 30 years from the date of deposit or for 5 years after the last request for the deposit at the depository or for the enforceable life of a U.S. patent that matures from this application, whichever is longer. The hybridomas will be replenished should they become non-viable at the depository.

A monoclonal receptor of the present invention can be produced by introducing, as by injection, the hybridoma into the peritoneal cavity of a mammal such as a mouse. Preferably, as already noted, syngenic or semi-syngenic mammals are used, as in U.S. Pat. No. 4,361,549, the disclosure of which is incorporated herein by reference. The introduction of the hybridoma causes formation of antibody-producing hybridomas after a suitable period of growth, e.g. 1-2 weeks, and results in a high concentration of the receptor being produced that can be recovered from the bloodstream and peritoneal exudate (ascites) of the host mouse. Although the host mice also have normal antibodies in their blood and ascites, the concentration of normal antibodies is typically only about five percent that of the monoclonal receptor concentration.

The monoclonal receptor present in the hybridoma supernatant can be used without purification or the receptor can be recovered from the ascites or serum of the mouse using standard techniques such as affinity chromatography using AD 169-infected cells bound to an immunosorbant such Sepharose 6B or 4B (Pharmacia Fine Chemicals, Piscataway, N.J.), followed by elution from the immunosorbant using an acidic buffer such as glycine hydrochloride at a pH value of about 2.5.

In the present studies, IgG fractions were obtained from mouse ascites by precipitation with 45 percent saturated ammonium sulfate followed by chromatography on DEAE-Sephacel with sodium chloride elution. The fraction that was eluted with 100 mM salt was dialyzed and concentrated. Stock solutions of antibody at 20 mg/ml were prepared in Tris-HCl (50 mM, pH 6.5). Protein concentrations were determined by the Lowry method. [*J. Biol. Chem.*, 193, 265 (1951)].

Example 6: Enzyme-linked Immunosorbent Assay (ELISA)

The binding of ligands and the effect of chemical modification were assayed by ELISA with antibody at a fixed concentration in the range of its titer, and varying the reagent or ligand concentration. Inhibition is reported if the titer is reduced 50 percent at less than a 1000:1 ratio of reagent to hapten.

Assays were performed in flat-bottom polyvinyl microtiter plates (Dynatech, Alexandria, Va.). The wells were coated with a solution comprising analog-ligand bound to BSA as the antigen ligand in phosphate buffered saline (PBS) using 50 microliters of solution per well. The ligand was coated at 1 microgram per milliliter. The plates were then incubated overnight at 37 degrees C. in a dry oven. The dried plates were stored at 4 degrees C. until use. Prior to the ELISA assay, dried plates were rehydrated by two washes of 2 minutes each with 10 millimolar (mM) PBS, pH 7.4, containing 0.1 percent polyoxalkylene (20) sorbitan monolaurate (Tween 20) and 0.02 percent Thimerosal (sodium ethylmercurithiosalicylate), (Sigma, St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for 1 hour at 4 degrees C. on a gyroshaker to contact the monoclonal antibody-containing supernatant with the bound analog-ligand. Following two washes of 2 minutes each, 50 microliters of peroxidase-labeled goat anti-mouse IgG+IgM (Tago, Burlingame, Calif.), diluted 1:1000, were added to each well, and the reaction mixture was incubated at 4 degrees C. for 1 hour to bind the labeled antibody to bound monoclonal antibody.

The substrate used to assay bound peroxidase activity was prepared just prior to use and consisted of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution were added to each well and color was allowed to develop for 15 minutes in the dark. Color development was stopped by adding 25 microliters of 4 molar (M) $H_2SO_4$ to each well and the optical density at 492 nanometers (nm) was measured with a Multiskan ELISA plate reader. Polyclonal antibodies raised to the above analog-ligand were observed to immunoreact (bind) to the analog-ligand.

Example 7: Comparative Kinetic Studies

A first composition was prepared that contained about 0.5 mM of a reactant ligand of formula I where R is methyl (phenyl 6-acetamido-5-hydroxyhexanoate) as substrate and 5 uM of a non-specific monoclonal antibody designated 24E12 in aqueous 50 mM phosphate as aqueous medium. This first composition was utilized as a control. A second composition was prepared that contained the same amount of reactant ligand substrate and 5 uM receptor 24B11 as a lactone synthase. A third composition was prepared identical to the second composition but further containing 20 uM of 2-phenoxy-2-oxo-6-(acetamidomethyl)-1,2-oxaphosphorinane (analog-ligand of formula II where R is methyl) as inhibitor.

The three compositions were maintained at room temperature and aliquots from each were taken at intervals to ascertain the concentration of substrate ligand remaining in each composition. Assays were carried out using HPLC (Hitachi) with a solvent containing 20 percent acetonitrile, 79.9 percent water and 0.1 percent trifluoroacetic acid, using a flow rate of 1.5 ml per minute. The detector was set at 225 nm. A C18 reverse phase column using Vidac 218TP54 as the solid phase was used.

Figure 2:
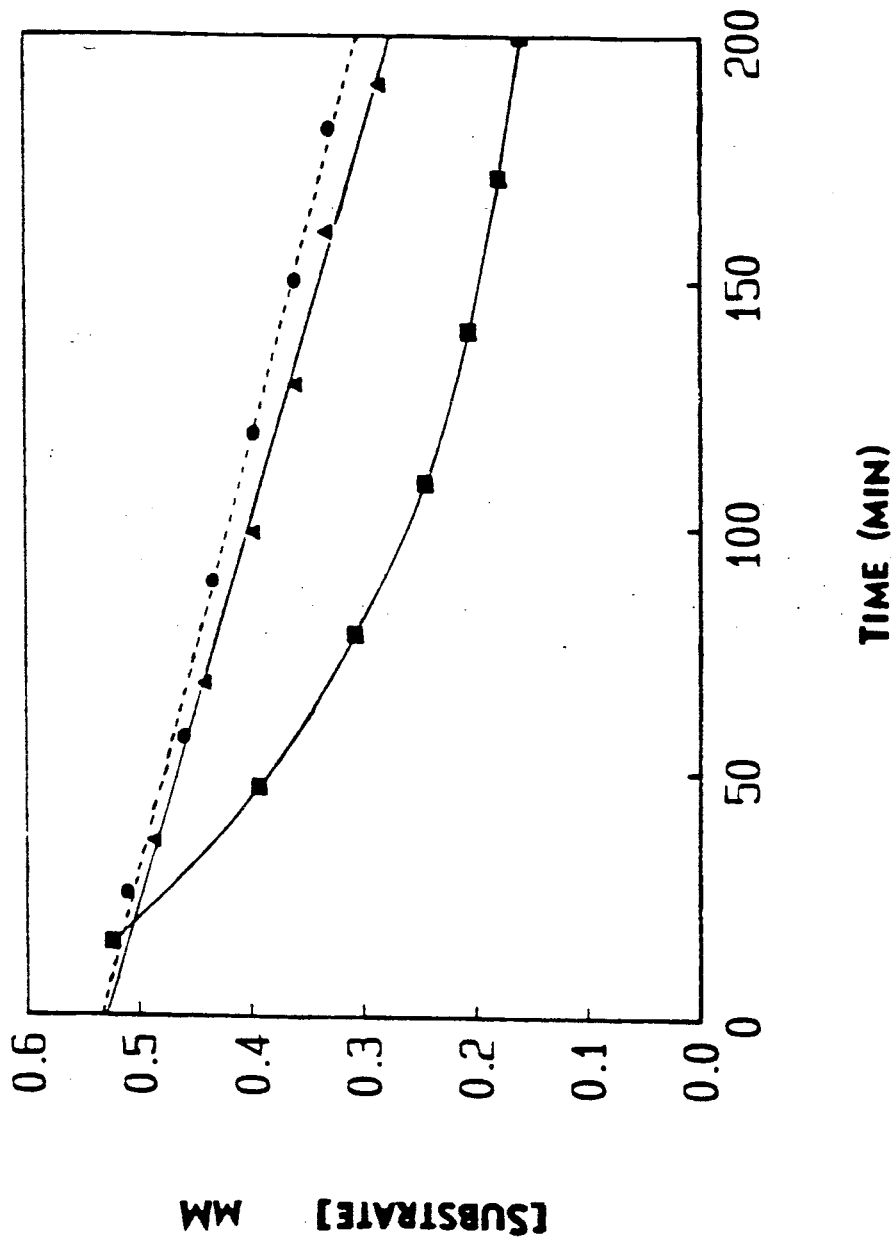
FIG. 2 is graph showing the decrease of reactant ligand capable of forming a lactone shown in FIG. 1 (substrate) in reaction media over time in minutes (min.) in the presence of (i) monoclonal antibody (Mab) 24B11 (closed squares), (ii) a control, non-catalytic monoclonal antibody (closed circles), and (iii) Mab 24B11 plus the immunizing analog-ligand derivative (formula II, where R is methyl) as a competitive inhibitor (closed triangles). The reactant ligand substrate was initially present at about 0.5 millimolar (mM) in a 50 mM phosphate buffer (pH 7.0). The Mab 24B11 or control monoclonal were present at 5 micromolar (uM), and the inhibiting analog-ligand derivative was present at 20 uM. The decrease in substrate concentration was determined by high performance liquid chromatography (HPLC).

As can be seen from examination of the data of FIG. 2, the concentration of substrate ligand in above Compositions 1 (control) and 3 (substrate plus inhibitor) decreased at substantially identical rates. The decrease in substrate ligand in Composition 2 that contained the lactone synthase and no inhibitor decreased much more rapidly until about one-half of the substrate was consumed, and thereafter decreased at a rate similar to that of Compositions 1 and 3. (The background decreases in substrate in Compositions 1, 2 and 3 are thought to be due to non-specific hydrolysis of the phenyl ester.)

Since the substrate was present at a one hundred-fold excess over the receptor, and since at least one-half of the substrate was consumed relatively rapidly, the results shown in FIG. 2 indicate that the reaction involving the receptor was greater than stoichiometric and that true catalysis with turn over of the receptor catalyst with synthase activity was observed.

A likely explanation for the relatively rapid decrease to about one-half the initial concentration of substrate followed by the background substrate decrease is that the receptor synthase binds to the ligand substrate and catalyzes the lactone-forming reaction stereospecifically. Thus, the ligand has an asymmetric carbon atom at the 5-position where the hydroxyl, hydrogen and methylene acetamido groups are bonded to the chain; i.e., the alpha-carbon of the alcohol portion of the molecule. As a consequence, the ligand substrate exists as an enantiomeric pair. A similar enantiomeric pair exists for the analog-ligand utilized to induce production of the receptor lactone synthase.

If the receptor lactone synthase 24B11 secreted by hybridoma 24Bl1 bound only one of the enantiomers of both the immunizing analog-ligand and substrate ligand, but not to the other enantiomer of either, it would be expected to catalyze lactone formation only by the substrate ligand to which it bound. Since each enantiomer constitutes one-half of the concentration of the enantiomeric pair, lactone formation of the bound enantiomer would be expected to be stereospecific and utilize only one-half of the admixed substrate ligand as is observed.

A schematic representation of the lactone synthase-catalyzed reaction illustrated for one enantiomer of the substrate ligand and one immunizing analog-ligand that is an analog to the lactone-forming transition state is shown in FIG. 1, using usual stereochemical depictions for chemical bonds. As is seen from that Figure, one enantiomer of the substate ligand (shown on the left) can form a transition state (shown in the brackets in the upper center of the Figure) that has a stereochemistry substantially identical to that of the analog-ligand (shown in brackets in the lower center). The lactone product (shown on the right of the Figure) is a single stereoisomer that retains the configuration of the ligand enantiomer that was bound and is shown on the left.

Example 8: Reaction Kinetics

Further kinetic determinations were made using the substrate ligand, monoclonal receptor lactone synthase and inhibitor of Example 7. Here, the receptor was present at a concentration of 2 uM from a Lowry assay and a presumed molecular weight of 150,000 daltons for an IgG antibody, along with 20–100 uM of the reactant ligand (substrate ligand) and 0.25 uM or 0.50 uM inhibitor, where used.

Phenol release from the substrate ligand was determined spectrophotometrically at 271 nm, and initial rates as a function of substrate concentration followed Michaelis-Menten kinetics consistent with the reaction sequence shown in the upper portion of FIG. 3. The lower portion of FIG. 3 shows Lineweaver-Burk plots for the inverse of intial rates (1/V) versus the inverse of the substrate ligand concentration (1/[S]). Relevant kinetic parameters in the presence and absence of the catalytic lactone synthase molecule are shown in Table 1, below, and indicate a rate acceleration of 167-fold.

TABLE 1

| Kinetic Parameters | | | | | |
|---|---|---|---|---|---|
| $K_m$* (uM) | $K_i$ (uM) | $V_{max}$ (uM/min) | $k_{cat}$ (1/min) | $k_{uncat}$ (1/min) | $k_{cat}/k_{uncat}$ |
| 76 | 0.25 | 0.99 | 0.50 | 0.003 | 167 |

*In the absence of binding by the unreactive enantiomer of the substrate ligand, $K_m$ is about 38 uM for the reactive enantiomer of the substrate ligand.

Control reactions were run to confirm that the catalytic activity observed was a property of the lactone synthase, 24B11, and not a contaminating esterase. It was found that neither the hydrolytically more labile coumarin ester of the substrate ligand nor coumaryl 5-hydroxypentanoate, which lacks the acetamidomethyl group of the substrate that can act as a recognition element, were substrates for catalysis. Another receptor designated 24E12 bound to the immunizing analog-ligand but did not catalyze liberation of phenol from the substrate ligand.

The reaction of the lactone synthase 24B11 with the substrate was lineary competitively inhibited by the addition of the N-acetyl derivative of the analog-ligand as can be seen from the before-mentioned Lineweaver-Burk plots of FIG. 3. The rate constant for that inhibition, $K_i$, was found to be 0.25 uM.

Example 9: Lactone Formation is Stereospecific

The data in Example 7 indicated that only about one-half (about 50 percent) of the added substrate was consumed relatively rapidly to release phenol, whereas the remaining phenol was liberated at a rate similar to that observed in the absence of the receptor synthase molecule. A second aliquot of substrate ligand was admixed with the reaction mixture after the first, relatively fast portion of the reaction was complete. That second admixture again resulted in a relatively rapid about 50 percent depletion of reactant ligand substrate, with the second depletion occurring at about the same rate as the first depletion. These results are shown in FIG. 4, wherein the first reactant ligand admixture is shown at point A, and the second is shown at point B.

Introduction of further receptor synthase 24B11 was without effect. Injection of an aliquot of pheonl (0.5 equivalents of the reactant ligand) provided the expected absorbance increase.

These results indicate the there was not inhibition of the reaction by one of its products, phenol, and also that phenol absorption was not somehow being masked. Furthermore, HPLC analysis of the reaction medium just after the relatively fast first phase was completed yielded about 50 percent of the reactant ligand.

Taken together, these results were consistent with a stereospecific receptor synthase-catalyzed reaction of one enantiomer of the reactant ligand substrate. There was no evidence for cyclization of the other enantiomer being catalyzed by the receptor synthase over the observed time course of about 30 minutes.

Example 10: Confirmation of Stereospecific Synthesis

To confirm that the lactone-forming reaction was catalyzed stereospecifically, the lactone product enantiomers were independently synthesized by treatment of 6-iodomethylvalerolactone [Shamma et al., *J. Am. Chem. Soc.*, 76:2315 (1954)] with sodium azide, followed by reduction in the presence of acetic anhydride. Extraction and chromatographic purification of the lactone permitted examination of enantiomeric purity by $^1$H NMR in the presence of a chiral lanthanide shift reagent, tris-[3-(heptafluoropropylhydroxymethylene)-d-camphorato]-europium (III), Eu(hfbc)$_3$, utilizing the acetamido function to bind the reagent. Sullivan, *Top. Steroreochem.*, 10:287 (1978).

Clear separation of each of the three single $^1$H NMR resonances for the protons of the CH$_3$CONH-substituent and of the sidechain CH$_2$ of the product lactone into two proton signals was obtained for both the receptor synthase-generated and chemically-synthesized lactone products. A portion of each spectrum is shown in FIG. 5.

The equivalence of peak areas for the synthetic sample as expected for a racemic modification validates the analytical method and indicates that the observed enantiomer excess (% major peak–% minor peak) generated by the receptor synthase-catalyzed cyclization was 66±4 percent.

That latter percentage can be corrected for the competing spontaneous cyclization reaction of the substrate under the study conditions using a computer simulation of the equation shown in the upper portion of FIG. 3 by employing the rate constants of Table 1. That computer simulation predicted that about 86 percent of the minor peak arose from the uncatalyzed, spontaneous reaction. It is noted that it is not necessary to introduce explicitly a term for the spontaneous hydrolysis of the lactone product since both enantiomers decay at identical rates, thus maintaining their relative ratio.

This analysis indicates that the stereospecificty of the receptor synthase-catalyzed lactone formation of the reactant ligand substrate favored one enantiomer in 94±8 percent excess, given the limits of the determinations. Thus, the work described herein documents the first antibody combining site-catalyzed bond-forming, as compared to hydrolytic, reaction; a cyclization reaction. That work more significantly also exemplifes the first demonstration of sterochemical control of a reaction course, as is so typical of an enzyme, catalyzed by an antibody combining site-containing molecule.

Example 11: Receptor-Mediated Separation of Stereoisomers.

The previous description discussed several manners by which useful receptor molecules could be used to separate stereoisomers from each other. This Example provides a step-by-step preparation of an affinity sorbant, affinity column and the separation of the most similar of stereoisomers, enantiomers.

Sepharose 4B-CL (Pharmacia Fine Chemicals, Piscataway, N.J.), a cross-linked agarose, is utilized as a water-insoluble matrix and is admixed with 2 M Na$_2$CO$_3$. The admixture is packed by centrifugation and the supernatant liquid is then discarded. Two volumes of 2M Na$_2$CO$_3$ are added to the packed Sepharose and that admixture is resuspended in a capped bottle.

Cyanogen bromide (CNBr) from a stock solution at a concentration of one gram per milliliter (g/ml) in water-free acetonitrile is added to the Sepharose 4B-CL suspension in an amount of 0.2 volumes of CNBr solution per volume of Sepharose 4B-CL (at 200 mg per ml Sepharose 4B-CL). The bottle is capped and the contents are mixed vigorously for a time period of 2–3 minutes at room temperature.

The suspension is poured onto a sintered glass funnel and washed under suction with: (1) ten volumes of 0.1 M NaHCO$_3$, pH 9.5; (2) 10 volumes of distilled water; and (3) 10 volumes of coupling buffer [(PBS); 0.02 M phosphate, 0.15 M NaCl, pH 7.5] to form CNBr-activated Sepharose 4B-CL. The activated Sepharose is removed from the filter and admixed with a solution containing monoclonal antibody 24Bll at 5 mg of antibody per original packed volume of Sepharose 4B-CL in coupling buffer to couple the antibody to the activated Sepharose. The coupling reaction is maintained for 2–4 hours at room temperature with tumbling mixing.

The antibody-coupled Sepharose is thereafer admixed with 1–2 volumes of 1 M ethanolamine, pH 8.0, to block any remaining reactive groups. The resulting admixture is maintained at room temperature for a time period of 2–4 hours. The resulting blocked 24Bll antibody-bound Sepharose water-insoluble affinity sorbant is thereafter packed in a column and thoroughly washed with the buffer utilized for separating the stereoisomers (below) until no further protein elutes from the column eluate.

The above procedure is that reported in *Antibody As A Tool*, Marchalonis and Warr eds., John Wiley & Sons, New York (1982), pages 89–91 wherein routine coupling efficiencies in excess of 80 percent are reported when offering IgG at a ratio of 5 mg/ml of Sepharose.

A column containing the blocked 24Bll antibody-bound Sepharose 4B-CL in an amount of 2 ml, based upon the original packed volume, is prepared using 25 mM phosphate buffer, pH 7.0, as the eluting buffer, and is washed as discussed before. One milliliter of a solution containing the enantiomeric analog-ligand of formula II where R is methyl at a concentration of 50 uM is added to the top of the column, and thereafter eluted therefrom. The original analog-ligand-containing solution is not optically active, whereas the eluate from the column is optically active, thereby demonstrating the separation of the enantiomeric stereoisomers.

The foregoing is intended as illustrative of the present invention but not limiting. Numerous variations and modifications may be effected without departing from true spirit and scope of the invention.

What is claimed is:

1. A method of forming a preselected carboxylic acid amide or ester product comprising the steps of:

admixing a reactant ligand structurally capable of forming the amide or ester product with an effective amount of an amide or ester synthase in an aqueous medium to form a reaction mixture, said reactant ligand containing a carbonyl group carbon atom and an amine or alcohol group structurally capable of forming the preselected carboxylic acid amide or ester, and said amide or ester synthase comprising a monoclonal receptor molecule containing an antibody combining site capable of catalyzing the formation of said preselected amide or ester, said combining site binding to:

(a) said reactant ligand, and (b) an analog-ligand structurally analogous to said preselected amide or ester product, said analog-ligand having a tetrahedrally bonded phosphorus atom located at the position occupied by the carbon atom of the carbonyl group of the preselected carboxylic amide or ester product, said tetrahedrally bonded phosphorus atom being bonded directly to:
  (i) the alpha-carbon atom of the acid portion of said analog-ligand by a single bond;
  (ii) a first oxygen atom that is doubly bonded to said phosphorus;
  (iii) a second oxygen atom that is bonded to said phosphorus atom by a single bond, and is singly bonded to a radical selected from the group consisting of hydrogen, $C_1$–$C_6$ lower alkyl, benzyl and phenyl; and
  (iv) a third oxygen atom or a nitrogen atom that is singly bonded to said phosphorus atom, and is also singly bonded to the alpha-carbon atom of the alcohol or amine portion of said analog-ligand; and
maintaining said reaction mixture for a time period sufficient for said preselected amide or ester product to form.

2. The method of claim 1 wherein said synthase is a lactam or lactone synthase.

3. The method of claim 1 wherein said synthase is an Fab portion of a monoclonal antibody.

4. The method of claim 1 wherein said synthase is an intact monoclonal antibody.

5. A method of forming a preselected enantiomeric carboxylic acid amide or ester product that contains an excess of one enantiomer over another enantiomer comprising the steps of:
  admixing an enantiomeric reactant ligand pair structurally capable of forming the enantiomeric amide or ester product with an effective amount of an amide or ester synthase in an aqueous medium to form a reactant mixture, said reactant ligand containing a carbonyl group carbon atom and an amine or alcohol group structurally capable of forming the preselected enantiomeric carboxylic acid amide or ester product, said amide or ester synthase comprising a monoclonal receptor molecule containing a antibody combining site capable of catalyzing the formation of said preselected enantiomer amide or ester product, said combining site binding to:
  (a) substantially only one enantiomer of said enantiomeric reactant ligand pair, and
  (b) a ligand structurally analogous to one enantiomer of a transition state leading to said preselected amide or ester product, the enantiomer of said analog-ligand that is bound by said combining site having a tetrahedrally bonded phosphorus atom located at the position occupied by the carbon atom of the carbonyl group of the carboxylic acid amide or ester product, said tetrahedrally bonded phosphorus atom being bonded directed to:
    (i) the alpha-carbon atom of the acid portion of said analog-ligand by a single bond;
    (ii) a first oxygen atom that is doubly bonded to said phosphorus;
    (iii) a second oxygen atom that is singly bonded to said phosphorus atom, and is singly bonded to a radical selected from the group consisting of hydrogen, $C_1$–$C_6$ lower alkyl, benzyl and phenyl; and
    (iv) a third oxygen atom or a nitrogen atom that is singly bonded to said phosphorus atom, and is also singly bonded to the alpha-carbon atom of the amine or alcohol portion of said analog-ligand; and
maintaining said reaction mixture for a time period sufficient for said preselected amide or ester product enantiomer to form.

6. The method of claim 5 wherein said amide or ester synthase is a lactam or lactone synthase.

7. The method of claim 5 wherein said synthase is an intact monoclonal antibody.

8. The method of claim 7 wherein said intact monoclonal antibody is secreted by hybridoma 24B11.

9. A method for carrying out a stereoselective synthesis to prepare a preselected product containing relatively more of one stereoisomer than another stereoisomer comprising the steps of:
  admixing a reactant ligand structurally capable of forming two stereoisomers of the preselected stereoisomeric product and an effective amount of a synthase molecule in a aqueous medium to form a reaction medium, said synthase molecule comprising a monoclonal receptor molecule containing an antibody combining site capable of stereospecifically catalyzing the formation of said product, said combining site binding to:
  (a) substantially only one stereoisomer of said reactant ligand, and
  (b) a ligand structurally analogous to a transition state leading to one of said product stereoisomers; and
maintaining said reaction mixture for a period of time sufficient for said stereoisomeric product to form.

10. The method of claim 10 wherein said synthase molecule is an amide or ester synthase.

11. An amide or ester synthase molecule comprising a monoclonal receptor molecule containing an antibody combining site capable of catalyzing the formation of an excess of one enantiomeric carboxylic acid amide or ester product over another enantiomer, said combining site binding to:
  (a) substantially only one enantiomer of an enantiomeric reactant ligand pair containing a carbonyl group carbon atom and an amine or alcohol group structurally capable of forming said preselected enantiomeric product, and
  (b) a ligand structurally analogous to one enantiomer of a transition state leading to said preselected amide or ester product, the enantiomer of said analog-ligand that is bound by said combining site having a tetrahedrally bonded phosphorus atom located at the position occupied by the carbon atom of the carbonyl group of the carboxylic acid amide or ester product, said tetrahedrally bonded phosphorus atom being bonded directly to:
    (i) the alpha-carbon atom of the acid portion of said analog-ligand by a single bond;
    (ii) a first oxygen atom that is doubly bonded to said phosphorus;
    (iii) a second oxygen atom that is singly bonded to said phosphorus atom, and is singly bonded to a radical selected from the group consisting of hydrogen, $C_1$–$C_6$ lower alkyl, benzyl and phenyl; and
    (iv) a third oxygen atom or a nitrogen atom that is singly bonded to said phosphorus atom, and is also singly bonded to the alpha-carbon atom of the amine or alcohol portion of said analog-ligand.

12. The amide or ester synthase molecule of claim 11 that is a lactam or lactone synthase.

13. The amide or ester synthase molecule of claim 12 that is an intact monoclonal antibody.

14. A synthase molecule comprising a monoclonal receptor molecule containing an antibody combining site capable of stereospecifically catalyzing the formation of a preselected product, said combining site binding to:
 (a) substantially only one stereoisomer of a reactant ligand structurally capable of forming two stereoisomers of said products; and
 (b) a ligand structurally analogous to a transition state leading to one of said product stereoisomers.

15. The synthase molecule of claim 14 wherein said product stereoisomers are enantiomers.

16. The synthase molecule of claim 14 wherein said product stereoisomers are geometric isomers.

* * * * *

UNITED STATES PATENT AND TRADEMARK OFFICE
CERTIFICATE OF CORRECTION

PATENT NO.     : 5,079,152                                    Page 1 of 1
DATED          : January 7, 1992
INVENTOR(S)    : Stephen Benkovic, Richard A. Lerner, Afonso Tramontano and Andrew D. Napper It is certified that error appears in the above-identified patent and that said Letters Patent is hereby corrected as shown below:

Column 1,
Line 6, insert:

-- This invention was made with government support under Contract No. GM 35318 from the National Institutes of Health and Contract No. DCB 8607352 from the National Science Foundation. The U.S. government has certain rights in the invention. --

Signed and Sealed this

Seventh Day of May, 2002

*Attest:*

*Attesting Officer*

JAMES E. ROGAN
*Director of the United States Patent and Trademark Office*